(12) United States Patent
McGiveron et al.

(10) Patent No.: US 11,166,724 B2
(45) Date of Patent: Nov. 9, 2021

(54) ADHESIVE DISTRIBUTION ON BUTTRESS FOR SURGICAL STAPLER

(71) Applicant: Ethicon LLC, Guaynabo, PR (US)

(72) Inventors: Omar Z. McGiveron, Cincinnati, OH (US); Pamela M. Ridgley, Lebanon, OH (US); Emily A. Schellin, Cincinnati, OH (US); Rebecca Spatholt, Cincinnati, OH (US); Heather Strang, West Chester, OH (US); Michael J. Vendely, Lebanon, OH (US); Jordan B. Wong, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 179 days.

(21) Appl. No.: 16/235,473

(22) Filed: Dec. 28, 2018

(65) Prior Publication Data
US 2020/0205820 A1    Jul. 2, 2020

(51) Int. Cl.
*A61B 17/064* (2006.01)
*A61B 17/072* (2006.01)
*A61B 17/00* (2006.01)

(52) U.S. Cl.
CPC .......... *A61B 17/07292* (2013.01); *A61B 2017/00951* (2013.01); *A61B 2017/07264* (2013.01); *A61B 2017/07271* (2013.01)

(58) Field of Classification Search
CPC ............ A61B 17/07207; A61B 17/072; A61B 17/07292; A61B 17/115–17/1155; A61B 2017/07221–2017/07285
See application file for complete search history.

(56) References Cited

U.S. PATENT DOCUMENTS

| 4,805,823 A | 2/1989 | Rothfuss |
| 5,415,334 A | 5/1995 | Williamson, IV et al. |
| 5,441,193 A * | 8/1995 | Gravener ......... A61B 17/07207 227/175.1 |
| 5,465,895 A | 11/1995 | Knodel et al. |

(Continued)

FOREIGN PATENT DOCUMENTS

| EP | 3 072 456 A1 | 9/2016 |
| WO | WO 2018/152118 A1 | 8/2018 |

OTHER PUBLICATIONS

U.S. Appl. No. 16/234,727, entitled "Surgical Stapler with Tissue Engagement Features Around Tissue Containment Pin," filed Dec. 28, 2018.

(Continued)

*Primary Examiner* — Kathleen S Holwerda
(74) *Attorney, Agent, or Firm* — Frost Brown Todd LLC

(57) ABSTRACT

A buttress assembly for use with a surgical stapled site has a buttress and an adhesive on one side of the buttress. The adhesive on the buttress is applied in a pattern where the adhesive extends near or along the edges of the buttress while a center region of the buttress remains relatively free of adhesive. The adhesive is applied such that it extends continuously along the buttress and has a height such that the adhesive creates a sealing attachment with an end effector. The adhesive can be applied in an uneven distribution such that there is more adhesive applied at one end of the buttress than the other. The adhesive can also be applied in a symmetric or asymmetric distribution about a longitudinal axis of the buttress.

20 Claims, 10 Drawing Sheets

(56) References Cited

U.S. PATENT DOCUMENTS

| | | |
|---|---|---|
| 5,597,107 A | 1/1997 | Knodel et al. |
| 5,632,432 A | 5/1997 | Schulze et al. |
| 5,673,840 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,503,257 B2 | 1/2003 | Grant et al. |
| 6,783,524 B2 | 8/2004 | Anderson et al. |
| 6,978,921 B2 | 12/2005 | Shelton, IV et al. |
| 6,988,650 B2 | 1/2006 | Schwemberger et al. |
| 7,000,818 B2 | 2/2006 | Shelton, IV et al. |
| 7,134,587 B2 | 11/2006 | Schwemberger et al. |
| 7,143,923 B2 | 12/2006 | Shelton, IV et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 | 4/2007 | Wukusick et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,524,320 B2 | 4/2009 | Tierney et al. |
| 7,644,848 B2 | 1/2010 | Swayze et al. |
| 7,691,098 B2 | 4/2010 | Wallace et al. |
| 7,721,930 B2 | 5/2010 | McKenna et al. |
| 7,806,891 B2 | 10/2010 | Nowlin et al. |
| 8,141,762 B2 | 3/2012 | Bedi et al. |
| 8,210,411 B2 | 7/2012 | Yates et al. |
| 8,371,491 B2 | 2/2013 | Huitema et al. |
| 8,408,439 B2 | 4/2013 | Huang et al. |
| 8,453,914 B2 | 6/2013 | Laurent et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,579,990 B2 | 11/2013 | Priewe |
| 8,602,288 B2 | 12/2013 | Shelton, IV et al. |
| 8,616,431 B2 | 12/2013 | Timm et al. |
| 8,783,541 B2 | 7/2014 | Shelton, IV et al. |
| 8,800,838 B2 | 8/2014 | Shelton, IV |
| 8,801,735 B2 | 8/2014 | Shelton, IV et al. |
| 8,814,025 B2 | 8/2014 | Miller et al. |
| 8,820,605 B2 | 9/2014 | Shelton, IV |
| 8,844,789 B2 | 9/2014 | Shelton, IV et al. |
| 8,899,464 B2 | 12/2014 | Hueil et al. |
| 8,992,060 B2 | 4/2015 | Dassanayake et al. |
| 8,998,060 B2 | 4/2015 | Bruewer et al. |
| 9,101,359 B2 | 8/2015 | Smith et al. |
| 9,186,142 B2 | 11/2015 | Fanelli et al. |
| 9,198,644 B2 | 12/2015 | Balek et al. |
| 9,211,120 B2 | 12/2015 | Scheib et al. |
| 9,301,759 B2 | 4/2016 | Spivey et al. |
| 9,386,988 B2 | 7/2016 | Baxter, III et al. |
| 9,393,018 B2 | 7/2016 | Wang et al. |
| 9,398,911 B2 | 7/2016 | Auld et al. |
| 9,492,170 B2 | 11/2016 | Bear et al. |
| 9,517,065 B2 | 12/2016 | Simms et al. |
| 9,597,082 B2 | 3/2017 | Stokes et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,421 B2 | 12/2017 | Zerkle et al. |
| 9,848,871 B2 | 12/2017 | Harris et al. |
| 9,867,615 B2 | 1/2018 | Fanelli et al. |
| 9,913,642 B2 | 3/2018 | Leimbach et al. |
| 9,936,954 B2 | 4/2018 | Shelton, IV et al. |
| 9,999,408 B2 | 6/2018 | Boudreaux et al. |
| 10,045,780 B2 | 8/2018 | Adams et al. |
| 10,092,292 B2 | 10/2018 | Boudreaux et al. |
| D833,010 S | 11/2018 | Harris et al. |
| 10,123,798 B2 | 11/2018 | Baxter, III et al. |
| D836,198 S | 12/2018 | Harris et al. |
| D836,199 S | 12/2018 | Schowalter et al. |
| 10,349,939 B2 | 7/2019 | Shelton, IV et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2008/0169328 A1 | 7/2008 | Shelton |
| 2012/0241493 A1 | 9/2012 | Baxter, III et al. |
| 2013/0068816 A1 | 3/2013 | Vasudevan et al. |
| 2013/0075447 A1 | 3/2013 | Weisenburgh et al. |
| 2013/0146643 A1* | 6/2013 | Schmid ........ A61B 17/068 227/180.1 |
| 2013/0206813 A1 | 8/2013 | Nalagatla |
| 2014/0209658 A1* | 7/2014 | Skalla ........ A61B 17/1155 227/175.1 |
| 2014/0239037 A1 | 8/2014 | Boudreaux et al. |
| 2015/0351758 A1 | 12/2015 | Shelton, IV et al. |
| 2016/0089146 A1 | 3/2016 | Harris et al. |
| 2016/0278774 A1* | 9/2016 | Shelton, IV ........ A61B 17/068 |
| 2017/0027571 A1 | 2/2017 | Nalagatla et al. |
| 2017/0049444 A1 | 2/2017 | Schellin et al. |
| 2017/0055980 A1 | 3/2017 | Vendely et al. |
| 2017/0055981 A1* | 3/2017 | Vendely ........ A61B 17/07292 |
| 2017/0055982 A1 | 3/2017 | Zeiner et al. |
| 2017/0055986 A1 | 3/2017 | Harris et al. |
| 2017/0056016 A1 | 3/2017 | Barton et al. |
| 2017/0056017 A1 | 3/2017 | Vendely et al. |
| 2017/0056018 A1 | 3/2017 | Zeiner et al. |
| 2017/0086823 A1 | 3/2017 | Leimbach et al. |
| 2017/0086837 A1 | 3/2017 | Vendely et al. |
| 2017/0086842 A1 | 3/2017 | Shelton, IV et al. |
| 2017/0119392 A1* | 5/2017 | Shelton, IV ..... A61B 17/07292 |
| 2018/0235610 A1 | 8/2018 | Harris et al. |
| 2018/0235611 A1 | 8/2018 | Harris et al. |
| 2018/0235619 A1 | 8/2018 | Harris et al. |
| 2019/0000481 A1 | 1/2019 | Harris et al. |

OTHER PUBLICATIONS

U.S. Appl. No. 16/234,740, entitled "Surgical Stapler with Sloped Staple Deck for Varying Tissue Compression," filed Dec. 28, 2018.

U.S. Appl. No. 16/235,488, entitled "Configuration of Buttress for Surgical Stapler," filed Dec. 28, 2018.

U.S. Appl. No. 16/235,503, entitled "Surgical Stapler Buttress with Tissue In-Growth Promotion," filed Dec. 28, 2018.

U.S. Appl. No. 16/235,522, entitled "Applicator for Surgical Stapler Buttress," filed Dec. 28, 2018.

U.S. Appl. No. 16/235,541, entitled "Packaging for Surgical Stapler Buttress," filed Dec. 28, 2018.

U.S. Appl. No. 16/235,617, entitled "Method of Applying Buttresses to Surgically Cut and Stapled Sites," filed Dec. 28, 2018.

U.S. Appl. No. 16/235,630, entitled "Curved Tip Surgical Buttress Applicator with Opening Feature for Curved Tip Alignment," filed Dec. 28, 2018.

U.S. Appl. No. 16/235,670, entitled "Curved Tip Surgical Buttress Assembly Applicator with Proximal Alignment Features," filed Dec. 28, 2018.

U.S. Appl. No. 16/235,681, entitled "Curved Tip Surgical Buttress Assembly Applicator with Compression Layer Pocket Features," filed Dec. 28, 2018.

Design U.S. Appl. No. 29/675,045, entitled "Surgical Stapler Deck with Tissue Engagement Cleat Features," filed Dec. 28, 2018.

Design U.S. Appl. No. 29/675,047, entitled "Surgical Stapler Deck with Tissue Engagement Recess Features," filed Dec. 28, 2018.

Design U.S. Appl. No. 29/675,168, entitled "Applicator for Surgical Stapler Buttress," filed Dec. 28, 2018.

Design U.S. Appl. No. 29/675,170, entitled "Buttress for Surgical Stapler," filed Dec. 28, 2018.

Design U.S. Appl. No. 29/675,172, entitled "Tray for Surgical Stapler Buttress Applicator," filed Dec. 28, 2018.

Design U.S. Appl. No. 29/675,197, entitled "Applicator for a Stapler Buttress," filed Dec. 28, 2018.

(56) References Cited

OTHER PUBLICATIONS

Design U.S. Appl. No. 29/675,199, entitled "Buttress Assembly for a Surgical Stapler," filed Dec. 28, 2018.
U.S. Appl. No. 62/209,041, entitled "Method and Apparatus for Applying a Buttress to End Effector of a Surgical Stapler," filed Aug. 24, 2015.
International Search Report and Written Opinion dated Mar. 20, 2020 for Application No. PCT/IB2019/060545, 12 pgs.
European Search Report, Extended, and Written Opinion dated Mar. 20, 2020 for Application No. EP 19219068.4, 7 pgs.
European Examination Report dated Jan. 18, 2021 for Application No. EP 19219068.4, 5 pgs.

* cited by examiner

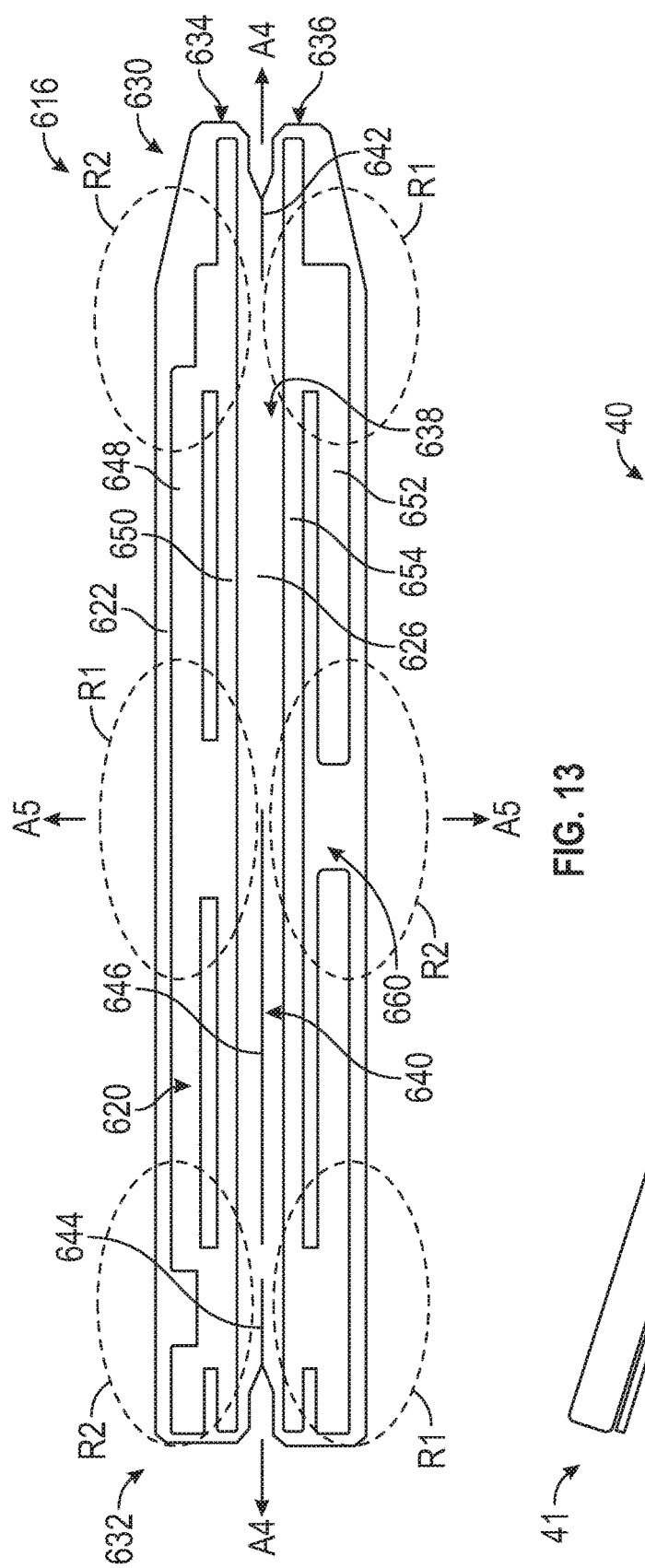
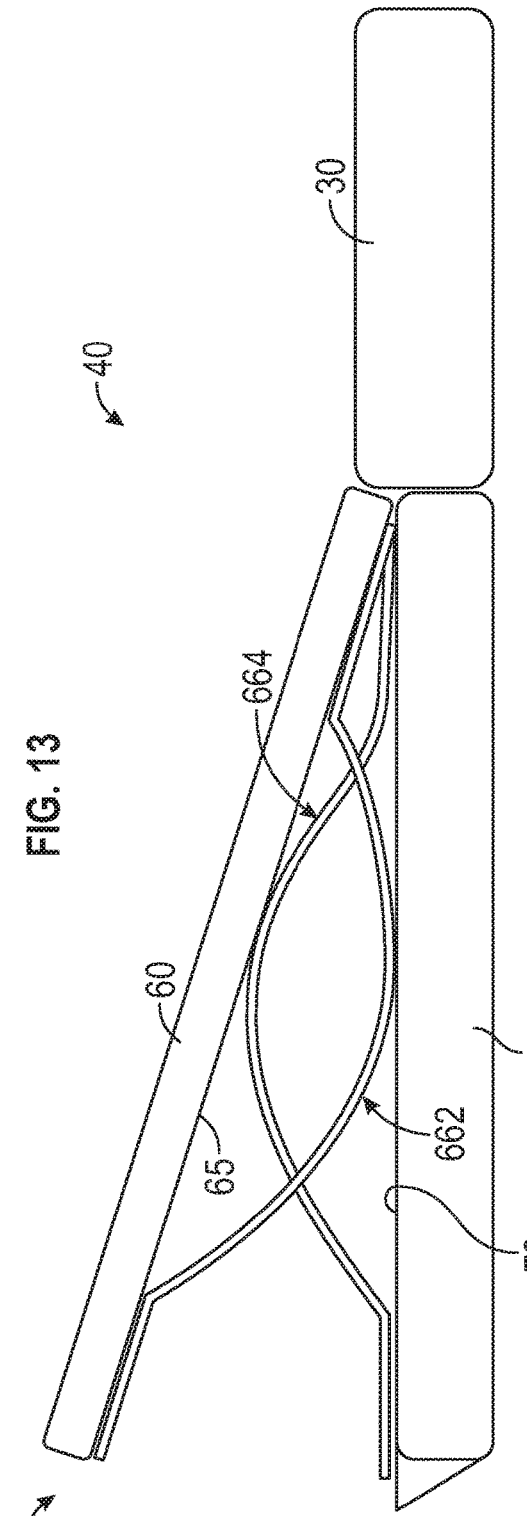
FIG. 13
FIG. 14

ADHESIVE DISTRIBUTION ON BUTTRESS FOR SURGICAL STAPLER

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Pat. No. 9,186,142, entitled "Surgical Instrument End Effector Articulation Drive with Pinion and Opposing Racks," issued Nov. 17, 2015; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,839,421, entitled "Jaw Closure Feature for End Effector of Surgical Instrument," issued Dec. 12, 2017; U.S. Pat. No. 9,867,615, entitled "Surgical Instrument with Articulation Lock having a Detenting Binary Spring," issued Jan. 16, 2018; U.S. Pat. No. 9,622,746, entitled "Distal Tip Features for End Effector of Surgical Instrument," issued Apr. 18, 2017; U.S. Pat. No. 10,092,292, entitled "Staple Forming Features for Surgical Stapling Instrument," issued Oct. 9, 2018; U.S. Pat. No. 9,795,379, entitled "Surgical Instrument with Multi-Diameter Shaft," issued Oct. 24, 2017; and U.S. Pat. No. 9,808,248, entitled "Installation Features for Surgical Instrument End Effector Cartridge," issued Nov. 7, 2017. The disclosure of each of the above-cited U.S. Patent Publications is incorporated by reference herein.

Additional surgical stapling instruments are disclosed in U.S. Pat. No. 8,801,735, entitled "Surgical Circular Stapler with Tissue Retention Arrangements," issued Aug. 12, 2014; U.S. Pat. No. 8,141,762, entitled "Surgical Stapler Comprising a Staple Pocket," issued Mar. 27, 2012; U.S. Pat. No. 8,371,491, entitled "Surgical End Effector Having Buttress Retention Features," issued Feb. 12, 2013; U.S. Pat. No. 9,597,082, entitled "Method and Apparatus for Sealing End-to-End Anastomosis" issued Mar. 21, 2017; U.S. Pat. No. 9,398,911, entitled "Rotary Powered Surgical Instruments with Multiple Degrees of Freedom," issued Jul. 26, 2016; U.S. Pat. Pub. No. 2013/0206813, entitled "Linear Stapler," published Aug. 15, 2013, now abandoned; U.S. Pat. Pub. No. 2008/0169328, entitled "Buttress Material for Use with a Surgical Stapler," published Jul. 17, 2008, now abandoned; U.S. Pat. No. 9,848,871, entitled "Woven and Fibrous Materials for Reinforcing a Staple Line," issued Dec. 26, 2017; U.S. Pat. No. 9,936,954, entitled "Devices and Methods for Sealing Staples in Tissue" issued Apr. 10, 2018; and U.S. Pat. Pub. No. 2016/0089146, entitled "Radically Expandable Staple Line" published Mar. 31, 2016, isssued as U.S. Pat. No. 10,426,476 on Oct. 1, 2019. The disclosure of each of the above-cited U.S. Patents, U.S. Patent Publications, and U.S. Patent Applications is incorporated by reference herein.

In some instances, it may be desirable to equip a surgical stapling instrument with a buttress material to reinforce the mechanical fastening of tissue provided by staples. Such a buttress may prevent the applied staples from pulling through tissue and may otherwise reduce a risk of tissue tearing at or near the site of applied staples.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 13 depicts a top plan view of another exemplary buttress assembly showing another exemplary asymmetric adhesive distribution; and FIG. 14 depicts a side elevation view of the end effector for a surgical stapler of FIG. 12 in an open position, showing the buttress assembly of FIG. 13 releasing from the jaws of the end effector.

Figure 1:
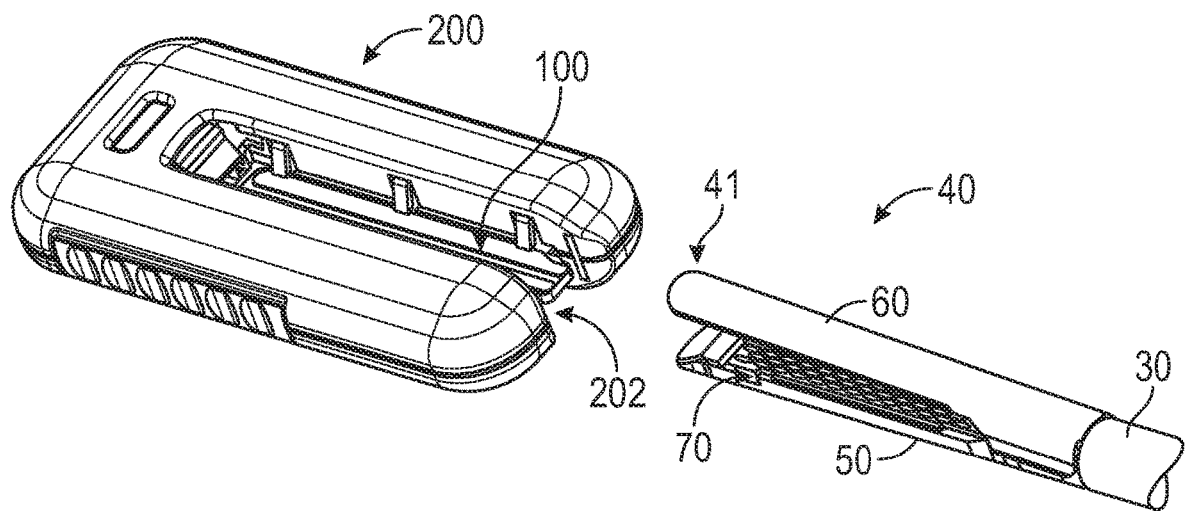
FIG. 1 depicts a perspective view of an exemplary end effector of a surgical stapler and an exemplary buttress applicator, with the end effector approaching the buttress applicator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Buttress Loading and Application

Figure 2:
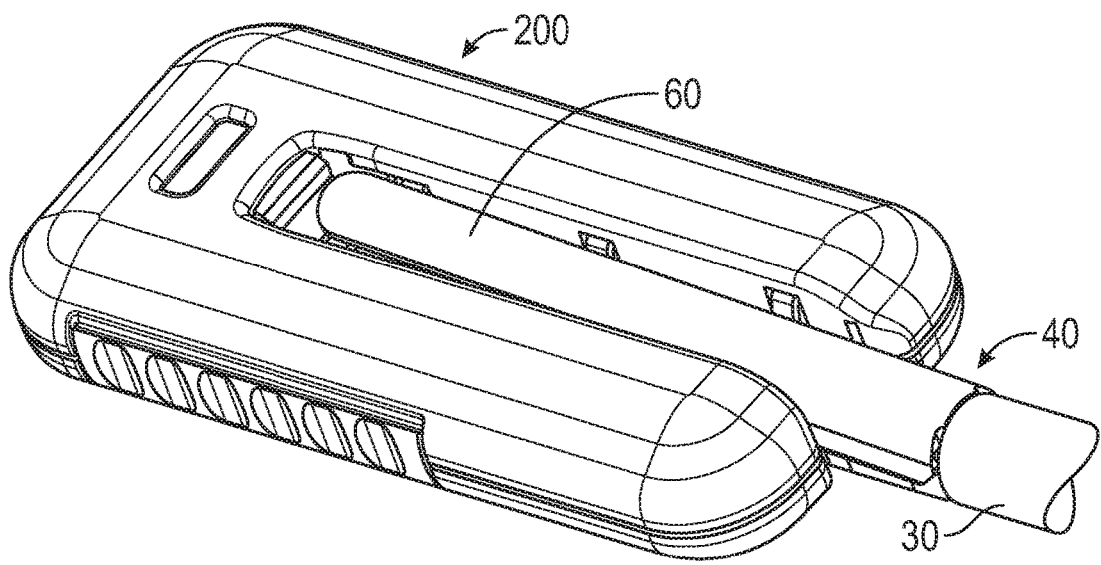
FIG. 2 depicts a perspective view of the end effector and the buttress applicator of FIG. 1, with the buttress applicator positioned in the end effector.

FIGS. 1 and 2 illustrate an exemplary end effector (40) configured to apply a buttress to a tissue site where a cutting and stapling operation is performed. End effector (40) is connected with a shaft assembly (30). End effector (40) comprises an anvil (60), a lower jaw (50), and a staple cartridge (70) received by lower jaw (50).

FIGS. 1 and 2 also illustrate an exemplary buttress applicator (200). Buttress applicator (200) is configured to selectively retain buttress assemblies (100, 110). In the present example, buttress assembly (100) is selectively retained on a top side of applicator (200) and buttress assembly (110) is selectively retained on a bottom side of applicator (200). In some other versions, applicator (200) can be configured such that only one buttress assembly (100, 110) is selectively retained by buttress applicator (200).

Figure 3:
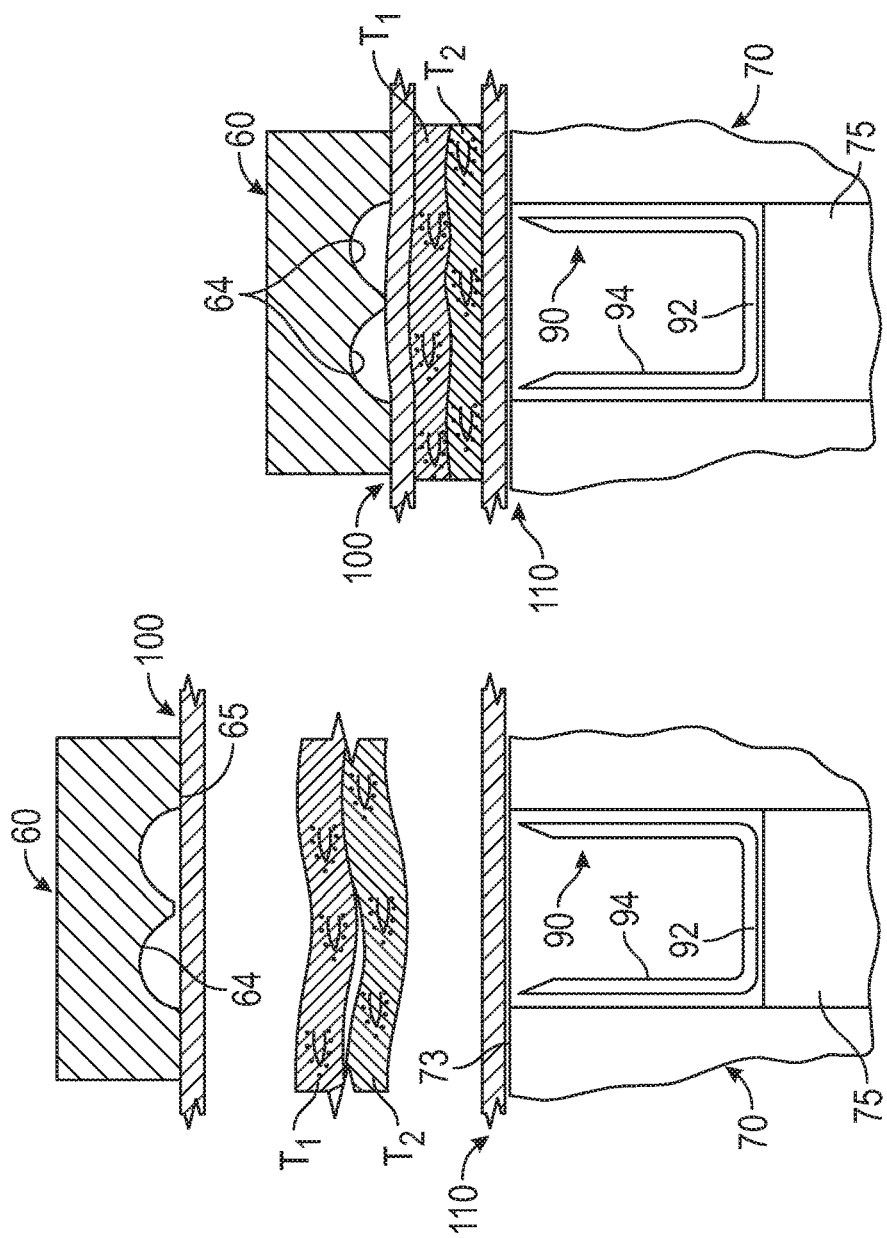
FIG. 3A depicts a cross-sectional end view of a portion of the end effector of FIG. 1 with the buttress assembly of FIG. 1 applied to the end effector, with tissue positioned between the buttresses in the end effector, and with the anvil in an open position.
FIG. 3B depicts a cross-sectional end view of the combined end effector and buttress assembly of FIG. 3A, with tissue positioned between the buttresses in the end effector, and with the anvil in a closed position.
FIG. 3C depicts a cross-sectional view of a staple and the buttress assembly of FIG. 3A having been secured to the tissue by the end effector of FIG. 1.

To use buttress applicator (200) to load end effector (40) with buttress assemblies (100, 110), the operator would first position applicator (200) and end effector (40) such that end effector (40) is aligned with an open end (202) of applicator (200) as shown in FIG. 1. The operator would then advance end effector (40) distally (and/or retract applicator (200) proximally) to position buttress assemblies (100, 110)

between anvil (60) and staple cartridge (70) as shown in FIG. 2. In order to load buttress assemblies (100, 110) on end effector (40), the operator may simply close end effector (40) by pivoting anvil (60) toward staple cartridge (70). Closure of end effector (40) results in the distal ends of anvil (60) and staple cartridge (70) bearing against retaining features of buttress applicator (200) that are configured to selectively retain buttress assemblies (100, 110) with buttress applicator (200). This contact deflects such retaining features of buttress applicator (200) to thereby permit contact between a surface of anvil (60) and buttress assembly (100) on one side of buttress applicator (200), and a surface of staple cartridge (70) and buttress assembly (110) on another side of buttress applicator (200). Buttress assemblies (100, 110) comprise an adhesive on their respective surfaces such that with end effector (40) clamping on both buttress assemblies (100, 110), buttress assemblies (100, 110) are adhered respectively to an underside of anvil (60) and a deck surface of staple cartridge (70). End effector (40) may then be re-opened (i.e., pivoting anvil (60) away from staple cartridge (70)) and pulled away from buttress applicator (200). With retaining features of applicator (200) disengaged from buttress assemblies (100, 110), end effector (40) may freely pull buttress assemblies (100, 110) away from buttress applicator (200) as end effector (40) is pulled away from buttress applicator (200). With buttress assemblies (100, 110) loaded on end effector (40), end effector (40) may then be used as described further below with reference to FIGS. 3A-4.

FIGS. 3A-3C show a sequence where an end effector (40) that has been loaded with buttress assemblies (100, 110) is actuated to drive staples (90) through two apposed layers of tissue ($T_1$, $T_2$), with buttress assemblies (100, 110) being secured to the same layers of tissue ($T_1$, $T_2$) by staples (90). In particular, FIG. 3A shows layers of tissue ($T_1$, $T_2$) positioned between anvil (60) and staple cartridge (70), with anvil (60) in the open position. As shown, anvil (60) comprises staple forming pockets (64). Buttress assembly (100) is adhered, via adhesive, to underside (65) of anvil (60); while buttress assembly (110) is adhered, via adhesive, to deck (73) of staple cartridge (70). Layers of tissue ($T_1$, $T_2$) are thus interposed between buttress assemblies (100, 110). Next, end effector (40) is closed, which drives anvil (60) to the closed position as shown in FIG. 3B. At this stage, layers of tissue ($T_1$, $T_2$) are compressed between anvil (60) and staple cartridge (70), with buttress assemblies (100, 110) engaging opposite surfaces of tissue layers ($T_1$, $T_2$). End effector (40) is then actuated, whereby a staple driver (75) drives staple (90) through buttress assemblies (100, 110) and tissue layers ($T_1$, $T_2$). As shown in FIG. 3C, crown (92) of driven staple (90) captures and retains buttress assembly (110) against layer of tissue ($T_2$). Deformed legs (94) of staple (90) capture and retain buttress assembly (100) against layer of tissue ($T_1$).

Figure 4:
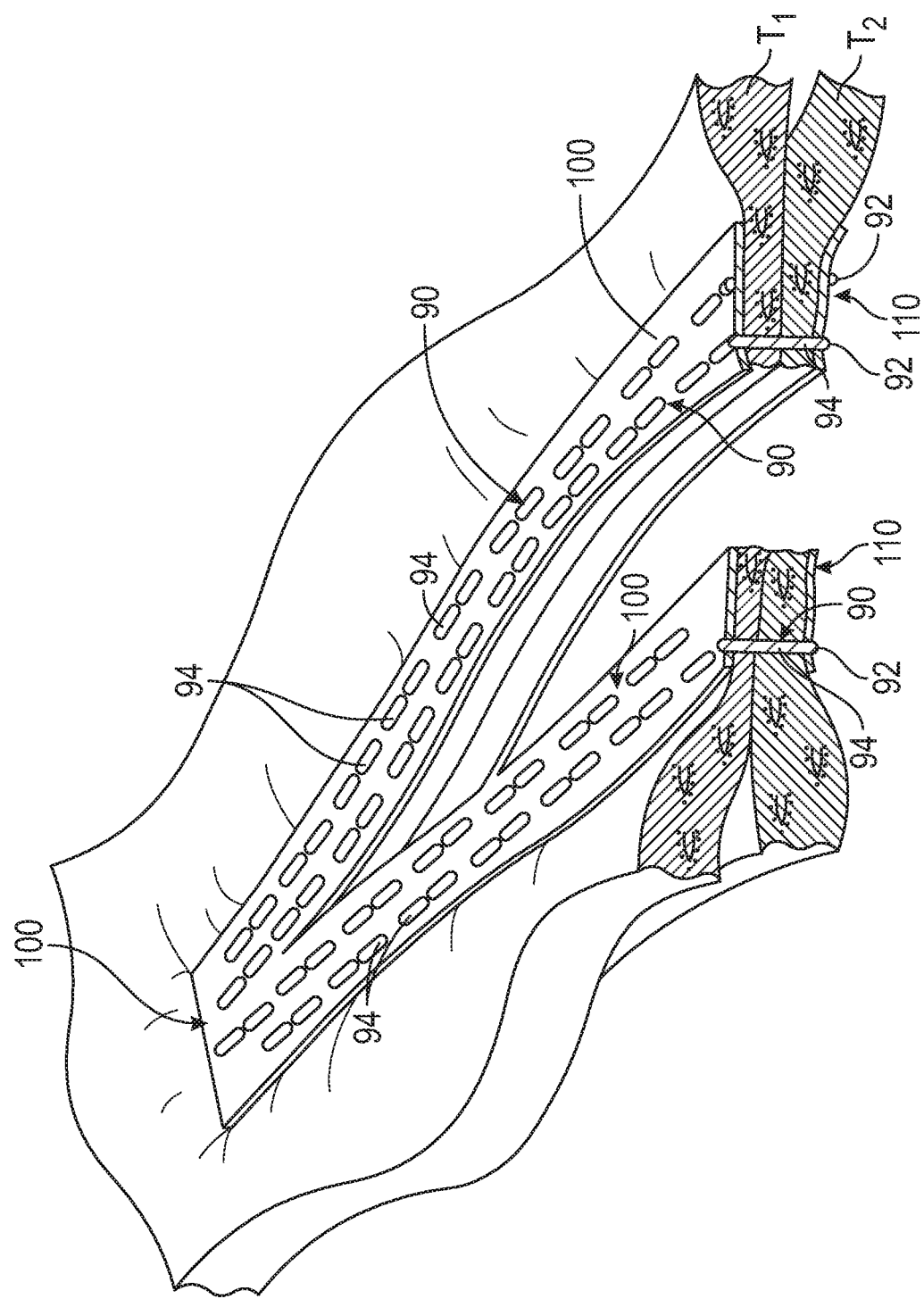
FIG. 4 depicts a perspective view of staples and the buttress assembly of FIG. 3A having been secured to the tissue by the end effector of FIG. 1.

It should be understood that a series of staples (90) will similarly capture and retain buttress assemblies (100, 110) against layers of tissue ($T_1$, $T_2$), thereby securing buttress assemblies (100, 110) to tissue ($T_1$, $T_2$) as shown in FIG. 4. As end effector (40) is pulled away from tissue (90) after deploying staples (90) and buttress assemblies (100, 110), buttress assemblies (100, 110) disengage end effector, such that buttress assemblies (100, 110) remain secured to tissue ($T_1$, $T_2$) with staples (90). Buttress assemblies (100, 110) thus provide structural reinforcement to the lines of staples (90). As can also be seen in FIG. 4, a knife member (not shown) passes through end effector (40) and in doing so also cuts through a centerline of buttress assemblies (100, 110), separating each buttress assembly (100, 110) into a corresponding pair of sections, such that each section remains secured to a respective severed region of tissue ($T_1$, $T_2$).

In the foregoing example, buttress assembly (100) is sized to span across the full width of underside (65) of anvil (60), such that a knife member (not shown) cuts through buttress assembly (100) during actuation of end effector (40). In some other examples, buttress assembly (100) is provided in two separate, laterally spaced apart portions, with one portion being disposed on underside (65) of anvil (60) on one half of anvil (60) and another portion being disposed on underside (65) of anvil (60) on the other half of anvil (60). In such versions, the knife member (not shown) does not cut through buttress assembly (100) during actuation of end effector (40).

Likewise, buttress assembly (110) may be sized to span across the full width of deck (73), such that the knife member (not shown) cuts through buttress assembly (110) during actuation of end effector (40). Alternatively, buttress assembly (110) may be provided in two separate, laterally spaced apart portions, with one portion being disposed on deck (73) on one half and another portion being disposed on deck (73) on the other half. In such versions, the knife member (not shown) does not cut through buttress assembly (110) during actuation of end effector (40).

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein.

II. Exemplary Buttress Applicator

Figure 5:
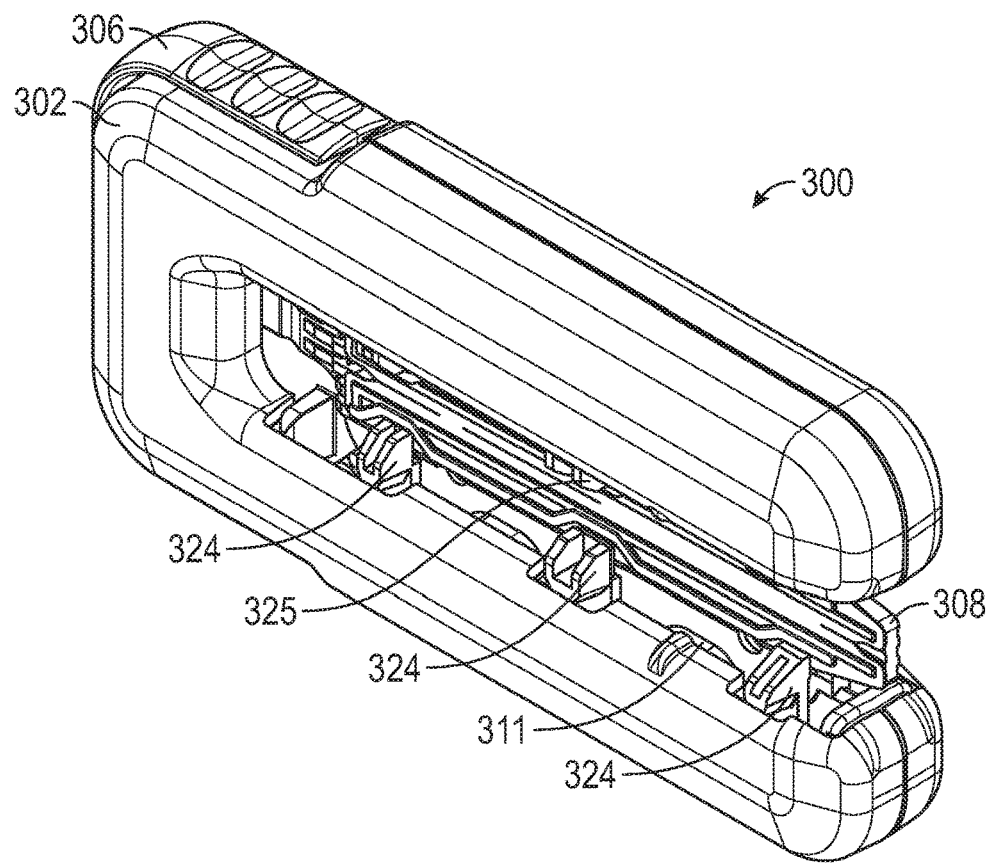
FIG. 5 depicts a perspective view of another exemplary buttress applicator usable with the end effector of FIG. 1.
Figure 6:
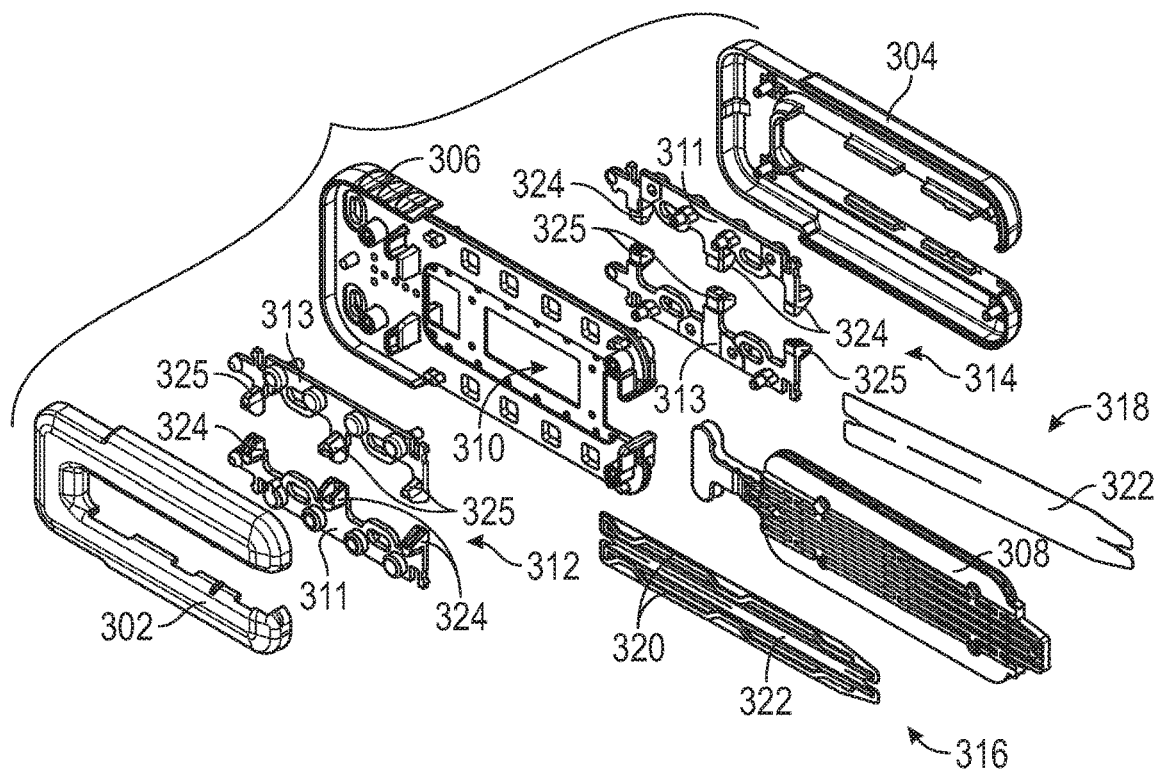
FIG. 6 depicts an exploded view of the buttress applicator of FIG. 5.

FIGS. 5 and 6 illustrate an alternate buttress applicator (300) for use with end effector (40). Buttress applicator (300) comprises a first housing portion (302) and a second housing portion (304). Each of housing portions (302, 304) connects with a frame (306). A compression pad (308) is configured to fit within a central portion (310) of frame (306). A first pair of clamp arms (312) are located on a first side of frame (306) between frame (306) and housing portion (302). A second pair of clamp arms (314) are located on a second side of frame (306) between frame (306) and housing portion (304). In the present version, clamp arms (312) comprise a left clamp arm (311) and a right clamp arm (313). Similarly, clamp arms (314) comprise a left clamp arm (311) and a right clamp arm (313). Buttress assemblies (316, 318) are located on respective sides of compression pad (308), and when buttress applicator (300) is fully assembled, pairs of clamp arms (312, 314) selectively retain buttress assemblies (316, 318) against compression pad (308). In the present example buttress assemblies (316, 318) are the same with each comprising an adhesive (320) located on a buttress (322) as will be described in greater detail below.

Buttress applicator (300) can be used with end effector (40) in the same manner as described above with respect to buttress applicator (200). For instance, buttress assemblies (316, 318) are loaded to end effector (40) in the same manner as described above where end effector (40) is moved to a closed or clamped position once anvil (60) and lower jaw (50) are positioned over central portion (310) of frame (308), e.g. as illustrated in FIG. 2. More specifically, the clamping action of end effector (40) when over buttress assemblies (316, 318) and compression pad (308) causes anvil (60) and staple cartridge (70) of lower jaw (50) to contact retention features (324) on left clamp arms (311) and retention features (325) on right clamp arms (313). This contact drives clamp arms (311, 313) laterally away from buttress assemblies (316, 318) thereby disengaging retention features (324, 325) from buttress assemblies (316, 318). With retention features (324, 325) disengaged, depending on the clamping orientation used with end effector (40), adhesive (320) of buttress assembly (316) contacts either underside (65) of anvil (60) or deck (73) of staple cartridge (70), while adhesive (320) of buttress assembly (318) contacts the other of underside (65) of anvil (60) or deck (73) of staple cartridge (70). This causes buttress assemblies (316, 318) to attach with end effector (40) and remain with end effector (40) as end effector is opened and moved away from buttress applicator (300). From this point, buttress assemblies (316, 318) may be applied to a cut and stapled tissue site as described above and illustrated with respect to FIG. 4.

III. Exemplary Buttress Assembly

Figure 7:
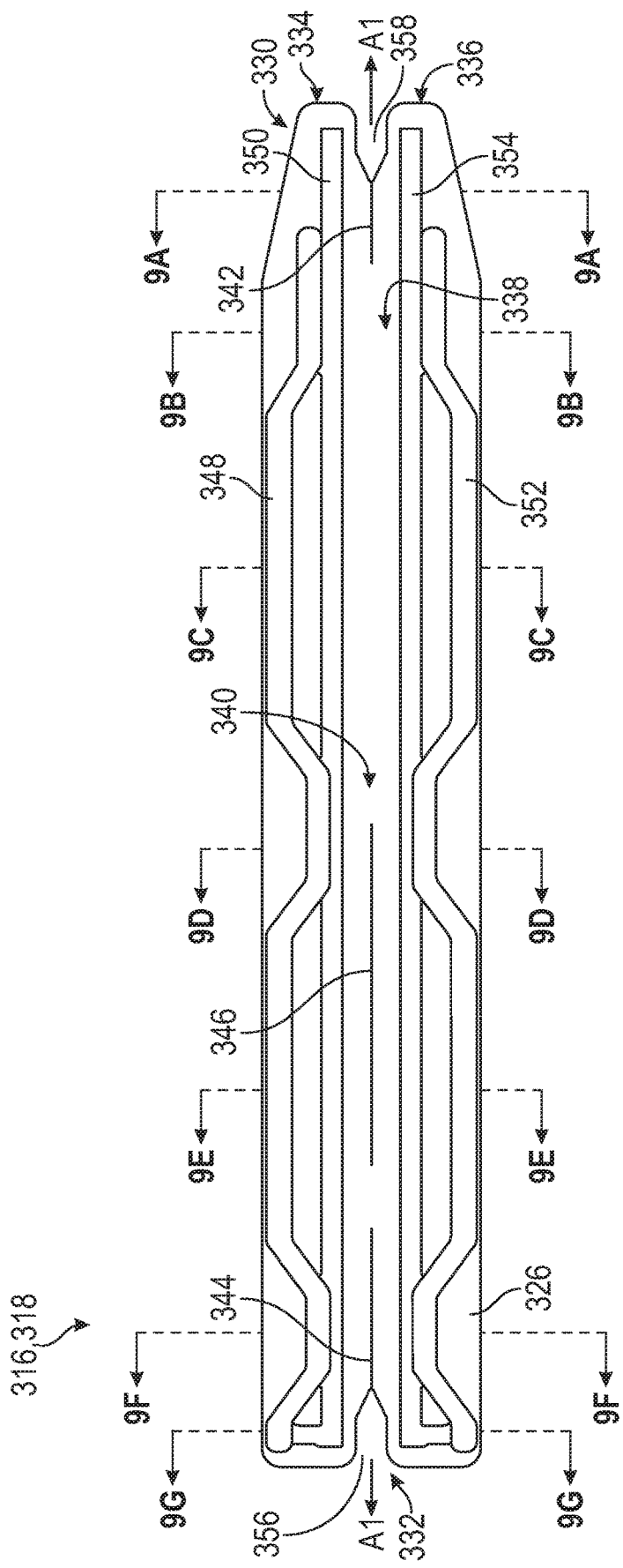
FIG. 7 depicts a top plan view of the buttress assembly of FIG. 5.

FIG. 7 illustrates buttress assembly (316), it being understood that buttress assembly (318) is identical. As mentioned, buttress assembly (316) comprises buttress (322) and adhesive (320) on one side of buttress (322). Buttress (322) comprises one or more layers of material. Where multiple layers are used the layers can be laminated together. In some examples buttress (322) comprises a mesh layer and one or more film layers laminated together. In some other examples buttress (322) comprises one or more film layers without a mesh layer. In view of the teachings herein, other various materials for one or more layers of buttress (322) will be apparent to those of ordinary skill in the art.

In the present example, buttress (322) is comprised of an absorbable material that is configured to be completed absorbed by the patient's body when used to reinforce a cut and staple site. In some examples, buttress (322) is comprised of polyglactin 910, which is 90% glycolide and 10% L-lactide. An example of polyglactin 910 is manufactured by Ethicon Inc. under the brand name Vicryl®. In view of the teachings herein, other absorbable synthetic materials for use with buttress (322) will be apparent to those of ordinary skill in the art.

A. Exemplary Adhesive Placement

Buttress (322) comprises a first surface (326) and a second surface (328) opposite to first surface (326). Buttress also includes a proximal end (330) and a distal end (332). As seen with reference to FIGS. 4 and 5, buttress assembly (316) is retained by applicator (300) such that when loading buttress assemblies (316, 318) to end effector (40), distal end (332) of buttress (322) aligns with a distal end (41) of end effector (40). With this configuration, buttress (322) defines a length extending from proximal end (330) to distal end (332). Buttress (322) further defines a longitudinal axis (A1) that extends between proximal end (330) and distal end (332). Buttress (322) includes a first edge region (334), a second edge region (336), and a center region (338) between and separating first edge region (334) and second edge region (336). Buttress (322) defines a width extending orthogonal to its length as defined above, where its width extends from first edge region (334) across center region (338) and through second edge region (336).

In the present example, adhesive (320) is applied onto first surface (326) of buttress (322). In some other versions of buttress assembly (316) adhesive (320) can be applied onto second surface (328) of buttress (322). Returning to the present example, adhesive (320) extends from proximal end (330) to distal end (332) of buttress (322). Moreover, in the present example, adhesive (320) extends continuously or in an uninterrupted manner. As shown in FIG. 7, adhesive (320) is located along first edge region (334) and second edge region (336), with center region (338) being substantially free of adhesive (320). As will be described further below, adhesive (320) is applied to buttress in a manner such that adhesive (320) comprises a height such that adhesive (320) is proud of buttress (322). The height of adhesive (320) is configured to facilitate adhesive (320) making good contact with either underside (65) of anvil (60) of end effector (40) or deck (73) of staple cartridge (70) of end effector (40) depending on the orientation of end effector (40) when loading buttress assembly (316).

The continuous nature of adhesive (320) along with the height of adhesive (320) act to seal the edges of buttress (322) to the part of end effector (40) to which buttress (322) attaches. For instance, where buttress assembly (316) is on anvil (60) side of end effector (40), the continuous adhesive (320) with its height creates a seal along the edges of buttress (322) of buttress assembly (316) where adhesive (320) contacts underside (65) of anvil (60). Similarly, where buttress assembly (318) is on staple cartridge (70) side of end effector (40), the continuous adhesive (320) with its height creates a seal along the edges of buttress (322) of buttress assembly (318) where adhesive (320) contacts deck (73) of staple cartridge (70). With this sealing attachment, in use the amount of moisture that can reach buttress assembly (316) is reduced. For instance, moisture is sealed out of the inside of buttress assembly (316), which keeps at least a portion of adhesive (320) free from moisture. By controlling moisture migration in this manner, buttress assemblies (316, 318) can have longer attachment times with end effector (40). This can give users greater lengths of time to position and manipulate end effector (40) before executing a cutting and stapling action, thereby applying buttresses (322) as reinforcing structures to the cut and stapled site.

Figure 9:
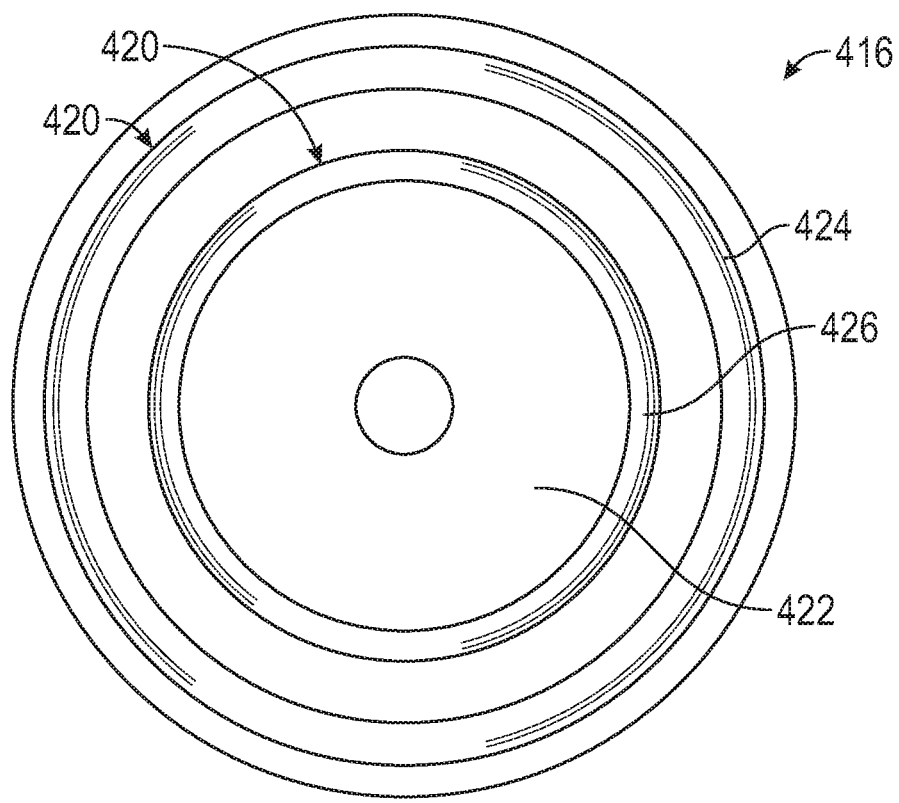
FIG. 9 depicts a top plan view of an exemplary buttress assembly configured for use with a circular surgical stapler.

Referring to FIG. 9, which shows exemplary buttress assembly (416), the sealing attachment discussed above can also apply to buttress assemblies configured for use with circular surgical staplers. For instance, buttress assembly (416) comprises a circular shape and is configured for use with a circular surgical stapler. Buttress assembly (416) comprises buttress (422) and adhesive (420). As shown, adhesive (420) is applied in a concentric circular pattern on buttress (422). In this manner, outer adhesive ring (424) creates sealing attachment with the end effector components of a circular stapler as those of ordinary skill in the art will understand in view of the teachings herein. This slows or prevents moisture from contacting a majority of buttress assembly (416), including inner adhesive ring (426), in the same or similar manner as described above with respect to buttress assemblies (316, 318).

B. Exemplary Adhesive Pattern and Distribution

Referring still to FIG. 7, and now also FIGS. 8A-8G, other details concerning buttress assemblies (316, 318) are described below relating to adhesive (320) and its pattern and amount. As shown in FIG. 7, center region (338) of buttress (322) comprises slits (340). In the illustrated version, slits (340) include a proximal slit (342), a distal slit (344), and an intermediate slit (346) between proximal and distal slits (342, 344). Slits (340) are configured to promote or facilitate cutting and separating buttress (322) into substantially equal halves during a cutting and stapling operation as discussed above. As shown in the present example, buttress assemblies (316, 318) comprise slits (342, 344) at both proximal end (330) and distal end (332) of buttress (322), where these slits (342, 344) extend all the way to the respective ends of buttress (322). This configuration helps ensure full cutting and separation of buttress (322) at its ends during a cut and staple sequence. Also in the present example, longitudinal axis (A1) passes through slits (340), and on each side of center region (338), adhesive (320) defines a pattern that is substantially symmetrical with the other side about longitudinal axis (A1).

Now considering adhesive (320) as applied to first edge region (334), adhesive (320) comprises a first bead (348) and a second bead (350). Each bead of adhesive (348, 350) extends generally from proximal end (330) of buttress (322) to distal end (332) of buttress (322). As shown in FIGS. 8A-8G, first bead of adhesive (348) partially overlaps second bead of adhesive (350) along at least a portion of a length of buttress (322). Still in other areas, first bead of adhesive (348) is spaced apart from second bead of adhesive (350) along at least a portion of a length of buttress (322). As shown best in FIG. 7, second bead of adhesive (350) extends further proximally compared to first bead of adhesive (348). Furthermore, first and second beads of adhesive (348, 350) extend distally to substantially the same extent relative to buttress (322).

Now considering adhesive (320) as applied to second edge region (336), adhesive (320) comprises a third bead (352) and a fourth bead (354). Each bead of adhesive (352, 354) extends generally from proximal end (330) of buttress (322) to distal end (332) of buttress (322). As shown in FIGS. 8A-8G, third bead of adhesive (352) partially overlaps fourth bead of adhesive (354) along at least a portion of a length of buttress (322). Still in other areas, third bead of adhesive (352) is spaced apart from fourth bead of adhesive (354) along at least a portion of a length of buttress (322). As shown best in FIG. 7, fourth bead of adhesive (354) extends further proximally compared to third bead of adhesive (352). Furthermore, third and fourth beads of adhesive (352, 354) extend distally to substantially the same extent relative to buttress (322). As mentioned above, first and second beads of adhesive (348, 350) are collectively symmetrical with third and fourth beads of adhesive (352, 354) about longitudinal axis (A1) defining a centerline of buttress (322).

Considering now adhesive (320) as applied at proximal and distal ends (330, 332) of buttress (322), in the present example, an uneven distribution of adhesive (320) is used. This uneven distribution of adhesive (320) comprises more adhesive at distal end (332) of buttress (322) than at proximal end (330) of buttress (322). In the present example, this is the case when comparing buttress (322) prior to cutting into halves or when comparing halves of cut buttress (322). This uneven distribution of adhesive (320) is created at least in part by second bead of adhesive (350) and fourth bead of adhesive (354) extending further proximally into proximal end (330) of buttress (322) compared to respective first bead of adhesive (348) and third bead of adhesive (352). And further on distal end (332) both first and second beads of adhesive (348, 350) and both third and fourth beads of adhesive (352, 354) extend to the same extent. This arraignment results in more adhesive (320) at distal end (332) compared to proximal end (330) of buttress (322). In examples like the present one where more adhesive (320) is present at distal end (332) of buttress (322), this helps buttress (322) stay attached and aligned to and with the respective parts of end effector (40) when aggressively manipulating end effector (40), i.e. when piercing through ostomies, sliding axially onto tissue, etc.

As mentioned, distal end (332) of buttress (322) aligns with distal end (41) of end effector (40). Because distal end (41) of end effector (40) is the first part of end effector (40) to contact tissue when positioning end effector (40), distal end (41) of end effector (40) can be subject to greater forces in use compared to the proximal end of end effector (40). Because of this, having stronger attachment of buttress assemblies (316, 318) at distal end (41) of end effector (40) can be beneficial to maintaining attachment and alignment of buttress assemblies (316, 318) with respective parts of end effector (40). One way to achieve such stronger attachment at distal end (332) of buttress assemblies (316, 318) is by having more adhesive placed at distal end (332) of buttress (322). More adhesive (320) can be achieved by a volume basis, a mass basis, a surface area or contact area basis, or an area density basis. In view of the teachings herein, other ways to provide for stronger attachment between buttress assemblies (316, 318) at their distal ends (332) and respective components at distal end (41) of end effector (40) will be apparent to those of ordinary skill in the art in view of the teaching herein.

In use, releasing of buttress (322) from end effector (40) is also a consideration. Buttress (322) should release from end effector (40) such that it is transferred to the tissue cut and stapled site so buttress (322) can provide structural reinforcement to the site. With the clamping action of the jaws of end effector (40), there is a large aperture or opening of distal end (41) after end effector (40) has been fired and is being opened to remove end effector (40) from a cut and stapled site. This motion of distal end (41) with the large aperture or opening enables release of buttress (322) from distal end (41) of end effector (40) even with buttress (322) initially having more adhesive (320) at its distal end (332) compared to its proximal end (330).

Figures 8A, 8B, 8C, 8D:
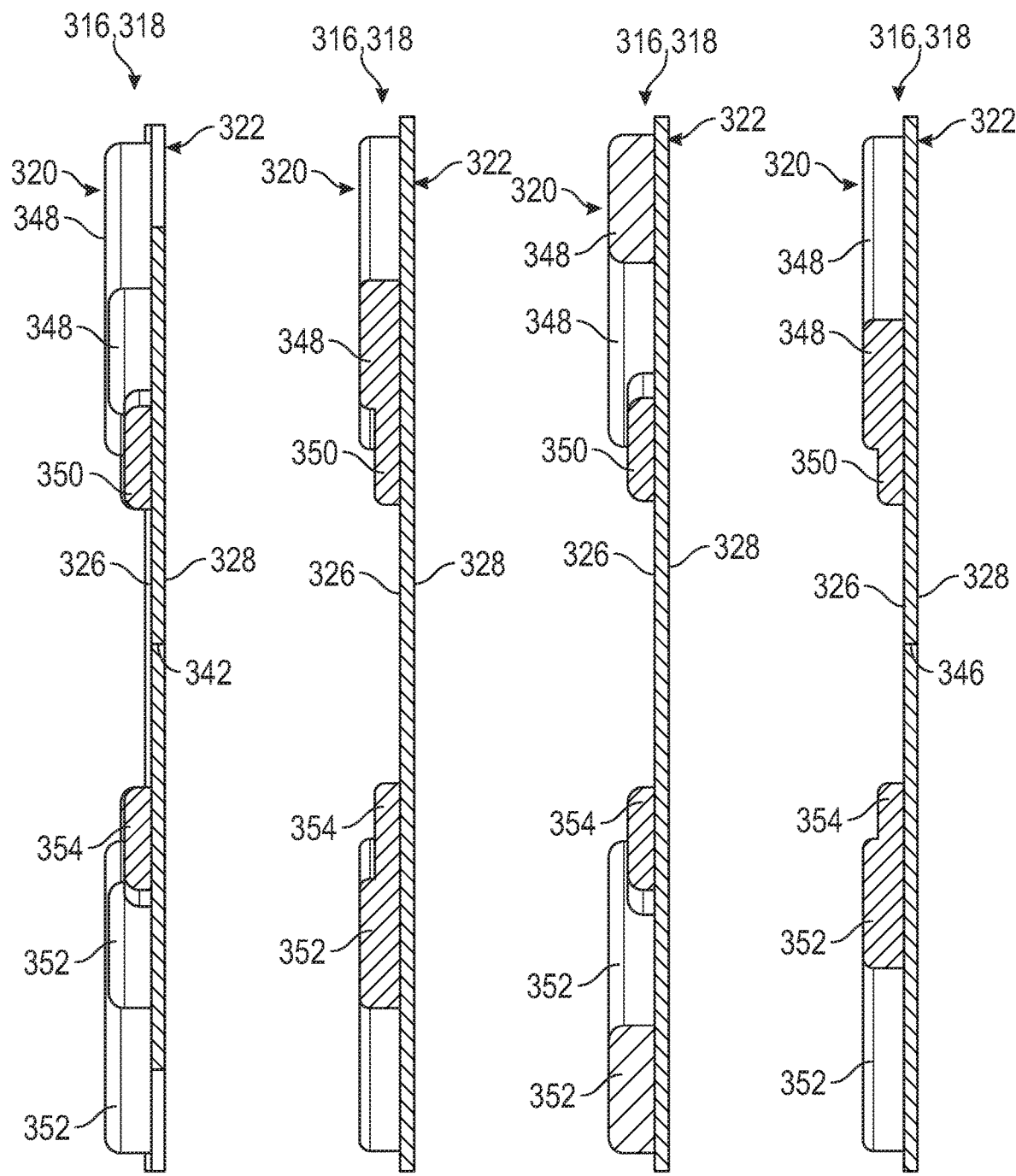
FIG. 8A depicts a cross section view of the buttress assembly of FIG. 7, taken along line 8A-8A of FIG. 7.
FIG. 8B depicts a cross section view of the buttress assembly of FIG. 7, taken along line 8B-8B of FIG. 7.
FIG. 8C depicts a cross section view of the buttress assembly of FIG. 7, taken along line 8C-8C of FIG. 7.
FIG. 8D depicts a cross section view of the buttress assembly of FIG. 7, taken along line 8D-8D of FIG. 7.

The described adhesive pattern and distribution above can be seen in FIGS. 8A-8G that show cross sections of adhesive (320) along the length of buttress (322). For instance, FIG. 8A is taken along proximal end (330) of buttress assembly (316). As shown in FIG. 8A, second and fourth beads of adhesive (350, 354) extend further proximally than first and third beads of adhesive (348, 352). Also evident from FIG. 8A is proximal slit (342). Furthermore, as shown in FIGS. 7 and 8A, buttress (322) comprises a taper at its proximal end (330), where a width of buttress (322) decreases as buttress (322) extends proximally.

FIG. 8B illustrates an area where first bead of adhesive (348) partially overlaps second bead of adhesive (350), and similarly an area where third bead of adhesive (352) partially overlaps fourth bead of adhesive (354). As shown in FIG. 8B as well as the other views of FIGS. 8A and 8C-8G, adhesive (320) is symmetrical about longitudinal axis (A1).

FIG. 8C illustrates how first bead of adhesive (348) is spaced apart from second bead of adhesive (350) when examining adhesive (320) further distally along the length of buttress (322). Similarly, third bead of adhesive (352) is spaced apart from fourth bead of adhesive (354). At the location shown in FIG. 8C, center region (338) lacks any slit in the present example.

FIG. 8D illustrates the adhesive pattern and distribution at an approximate middle of the length of buttress assemblies (316, 318). Here again, first bead of adhesive (348) partially overlaps second bead of adhesive (350), and similarly third bead of adhesive (352) partially overlaps fourth bead of adhesive (354). When comparing FIG. 8D with 8B, in the present example, the degree of adhesive overlap is greater at the approximate middle of the length of buttress assemblies (316, 318) as evident by the larger width of the overlap.

Figures 8E, 8F, 8G:
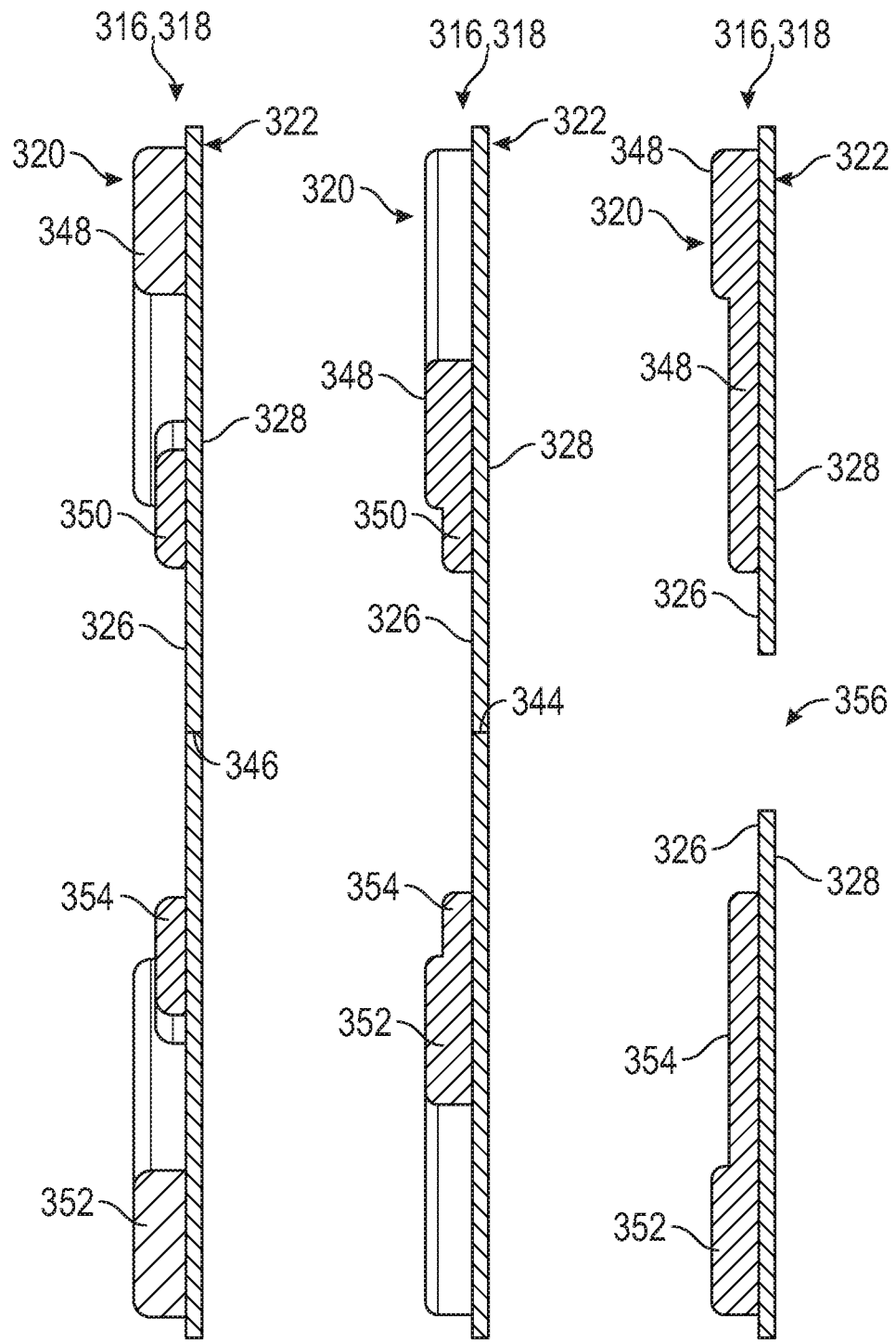
FIG. 8E depicts a cross section view of the buttress assembly of FIG. 7, taken along line 8E-8E of FIG. 7.
FIG. 8F depicts a cross section view of the buttress assembly of FIG. 7, taken along line 8F-8F of FIG. 7.
FIG. 8G depicts a cross section view of the buttress assembly of FIG. 7, taken along line 8G-8G of FIG. 7.

FIG. 8E illustrates a similar arrangement as shown in FIG. 8C. The only difference with FIG. 8E is that slit (346) splits buttress (322) into halves along the length shown in FIG. 8E, whereas center region (338) lacks any slit along the length shown in FIG. 8C.

FIG. 8F illustrates a similar arrangement as shown in FIG. 8D. The only difference with FIG. 8F is that center region (338) comprises distal slit (344) along the length shown in FIG. 8F, whereas center region (338) comprises intermediate slit (346) along the length shown in FIG. 8D.

FIG. 8G illustrates adhesive (320) at distal end (332) of buttress (322). As seen in FIGS. 7 and 8G, second bead of adhesive (350) extends away from center region (338) at distal end (332) of buttress (322). Similarly, fourth bead of adhesive (354) extends away from center region (338) at distal end (332) of buttress (322). In the present example, second bead of adhesive (350) extends away from center region (338) such that second bead of adhesive (350) connects with or contacts first bead of adhesive (348) at distal end (332) of buttress (322). Also, fourth bead of adhesive (354) extends away from center region (338) such that fourth bead of adhesive (354) connects with or contacts third bead of adhesive (352) at distal end (332) of buttress (322). As also shown in FIG. 8G, buttress (322) comprises a gap (356) at distal end (332), where gap (356) aligns with center region (338). Referring to FIG. 7, a gap (358) is also present at proximal end (330) in the present example.

C. Exemplary Adhesive Heights

Figure 10:
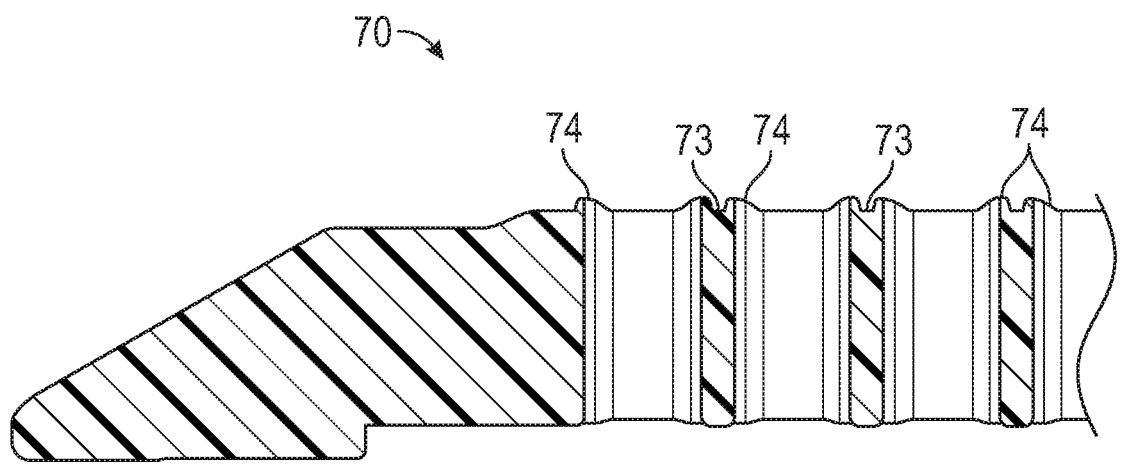
FIG. 10 depicts a cross section view of a staple cartridge of the end effector of FIG. 1.

As mentioned above adhesive height is a feature or attribute that facilitates attachment and release of buttress (322) with anvil (60) and staple cartridge (70) components of end effector (40). In this respect height of adhesive (320) is understood as the distance adhesive (320) protrudes from the surface of buttress (322) to which it is applied. In the present example, beads of adhesive (348, 350, 352, 354) have a minimum height. In one example, the minimum height is configured to approximate, match, or exceed the height of pocket extenders (74) on deck (73) of staple cartridge (70). FIG. 10 illustrates a cross section view of a version of staple cartridge (70) having pocket extenders (74). Pocket extenders (74) protrude above deck (73) of staple cartridge (70) and can assist in gripping tissue captured by end effector (40). By configuring adhesive beads (348, 350, 352, 354) with a minimum height that approximates, matches, or exceeds the distance that pocket extenders (74) protrude above deck (73), adhesive (320) can be in contact with the surface of pocket extenders (74) but also with the surface of deck (73) between pocket extenders (74). This provides for good attachment of one of buttress assemblies (316, 318) with staple cartridge (70) during the buttress loading process and increases retention of buttress (322) to this component of end effector (40) when working with and positioning end effector (40). While pocket extenders (74) are used with the version of staple cartridge (70) shown in FIG. 10, in other versions of staple cartridge (70) pocket extenders (74) are omitted such that deck (73) is flat with the exception of the openings for driving staples (90).

In one example, beads of adhesive (348, 350, 352, 354) have a height between about 0.010 inches (0.254 mm) and about 0.050 inches (1.27 mm). In another example, beads of adhesive (348, 350, 352, 354) have a height between about 0.016 inches (0.4064 mm) and about 0.030 inches (0.762 mm). In view of the teachings herein, other heights for beads of adhesive (348, 350, 352, 354) will be apparent to those of ordinary skill in the art.

In another example of a minimum adhesive height, beads of adhesive (348, 350, 352, 354) have a minimum height that is configured to approximate, match, or exceed the depth of staple forming pockets (64) of anvil (60). By way of reference, staple forming pockets (64) are illustrated in FIGS. 3A-3B. By configuring adhesive beads (348, 350, 352, 354) with a minimum height that approximates, matches, or exceeds the depth of staple forming pockets (64), adhesive (320) can be in contact with underside (65) of anvil (60) but also extend into staple forming pockets (64). This provides for good attachment of one of buttress assemblies (316, 318) with anvil (60) during the buttress loading process and increases retention of buttress (322) to this component of end effector (40) when working with and positioning end effector (40).

In some examples, like end effector (40) having anvil (60) and staple cartridge (70), the depth of staple forming pockets (64) of anvil (60) can be different from the distance that pocket extenders (74) protrude above deck (73) of staple cartridge (70). In such instances where buttress assemblies (316, 318) are identical, beads of adhesive (348, 350, 352, 354) can be configured such that the minimum height is based on the larger distance. For instance in an example where staple forming pockets (64) are shallower than pocket extenders (74)—such that staple forming pockets (64) have a depth that is less than the distance pocket extenders (74) protrude from deck (73)—beads of adhesive (348, 350, 352, 354) can be configured such that the minimum height is based on the distance pocket extenders (74) protrude above deck (73) as that is the greater distance compared with the depth of staple forming pockets (64) of anvil (60). Still in other versions, buttress assemblies (316, 318) could be configured differently in terms of adhesive heights to configure the adhesive heights specific to either the anvil side or staple cartridge side of the end effector. However, by setting the minimum adhesive height based on the greater distance, the good attachment and retention results can be obtained in a symmetric configuration that allows applicator (300) to be universal and not specific to any particular side of the end effector when loading a buttress assembly thereto.

In the present example where adhesive (320) is applied in beads, various adhesive heights can be achieved in a more efficient manner compared to applying a uniform spray of adhesive across the entire surface of buttress (322). This efficiency is realized both in terms of material usage and cost. Additionally, while the above examples show and describe adhesive height with respect to linear style buttress assemblies (316, 318), adhesive height can be controlled and configured in the same ways with circular buttresses such as buttress assembly (416) of FIG. 9.

D. Exemplary Asymmetric Adhesive Distributions

When loading buttress assemblies to an end effector and applying them to a tissue cut and stapled site, another consideration, besides good attachment and retention of the buttress assemblies with the end effector, is release of the buttress assemblies from the end effector after executing a cut and staple operation. For instance, if release is poor, buttress assemblies can adhere to the end effector instead of transferring to the tissue, or buttress assemblies can bunch or fold instead of laying flat and smooth against the tissue site. Referring now to FIGS. 11-14, buttress assemblies are shown that use asymmetric adhesive distributions to achieve both desired attachment and retention and also release of buttress assemblies.

Figure 11:
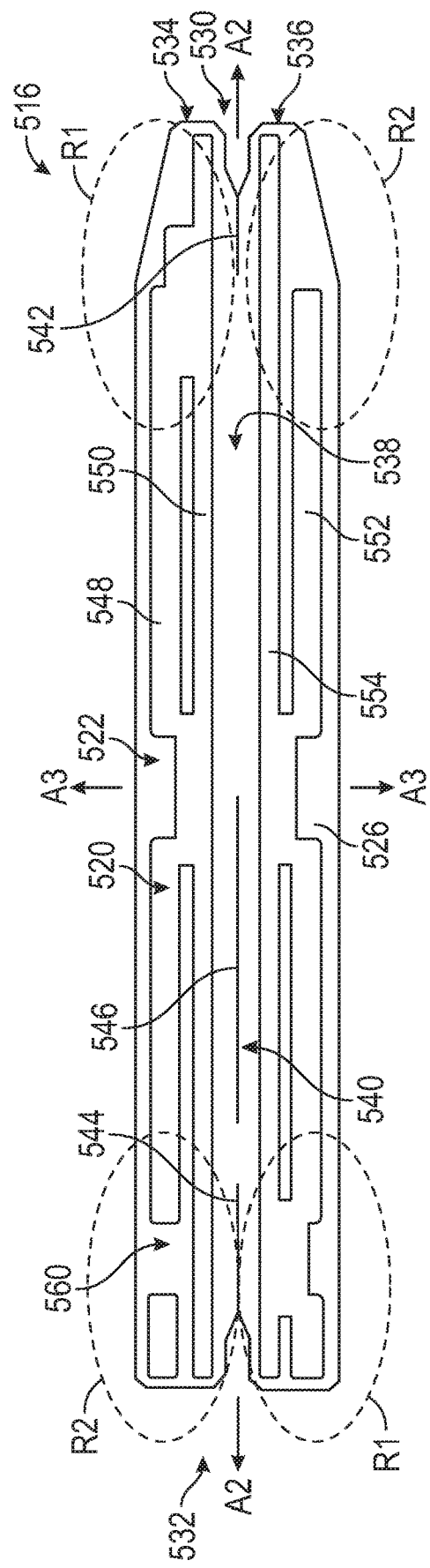
FIG. 11 depicts a top plan view of another exemplary buttress assembly showing an exemplary asymmetric adhesive distribution.

FIG. 11 illustrates a buttress assembly (516) having an asymmetric adhesive distribution. Buttress assembly (516) is configured similar to buttress assemblies (316, 318) described above, except with a different adhesive application pattern. Accordingly, two buttress assemblies (516) can be used in place of buttress assemblies (316, 318) described above. This includes being used in place of buttress assemblies (316, 318) with applicator (300) and end effector (40).

In the present example of FIG. 11, buttress assembly (516) comprises buttress (522) and adhesive (520) on one side of buttress (522). Buttress (522) comprises a first surface (526) and a second surface opposite to first surface (526). Buttress also includes a proximal end (530) and a distal end (532). As with buttress assemblies (316, 318) when buttress assembly (516) is attached with end effector (40) distal end (532) of buttress (522) aligns with a distal end (41) of end effector (40). With this configuration, buttress (522) defines a length extending from proximal end (530) to distal end (532). Buttress (522) further defines a longitudinal axis (A2) that extends between proximal end (530) and distal end (532). Buttress (522) includes a first edge region (534), a second edge region (536), and a center region (538) between and separating first edge region (534) and second edge region (536). Buttress (522) defines a width extending orthogonal to its length as defined above, where its width extends from first edge region (534) across center region (538) and through second edge region (536).

In the present example, adhesive (520) is applied onto first surface (526) of buttress (522). Adhesive (520) extends from proximal end (530) to distal end (532) of buttress (522). Moreover, in the present example, at least a portion of adhesive (520) extends continuously or in an uninterrupted manner. Adhesive (520) is located along first edge region (534) and second edge region (536), with center region (538) being substantially free of adhesive (520). As described above, adhesive (520) is applied to buttress in a manner such that adhesive (520) comprises a height such that adhesive (520) is proud of buttress (522). The height of adhesive (520) is configured to facilitate adhesive (520) making good contact with either underside (65) of anvil (60) of end effector (40) or deck (73) of staple cartridge (70) of end effector (40) depending on the orientation of end effector (40) when loading buttress assembly (516) onto end effector (40) using applicator (300).

The continuous nature of adhesive (520) along with the height of adhesive (520) act to seal the edges of buttress (522) to the part of end effector (40) to which buttress (522) attaches. With this sealing attachment, in use the amount of moisture that can reach buttress assembly (516) is reduced. By controlling moisture migration in this manner, buttress assembly (516) can have longer attachment times with end effector (40). This can give users greater lengths of time to position and manipulate end effector (40) before executing a cutting and stapling action, thereby applying buttresses (522) as reinforcing structures to the cut and stapled site.

Referring still to FIG. 11, center region (538) of buttress (522) comprises slits (540), which are structurally and functionally the same as slits (340) of buttress assemblies (316, 318). In the illustrated version, slits (540) include a proximal slit (542), a distal slit (544), and an intermediate slit (546) between proximal and distal slits (542, 544). In the present example, longitudinal axis (A2) passes through slits (540), and on each side of center region (538), adhesive (520) defines a pattern that is asymmetrical with the other side about longitudinal axis (A2). Adhesive (520) is further asymmetrical about a lateral axis (A3) that extends orthogonal relative to longitudinal axis (A2) through a midpoint of buttress assembly (516) as measured between proximal and distal ends (330, 332).

Now considering adhesive (520) as applied to first edge region (534), adhesive (520) comprises a first bead (548) and a second bead (550). Each bead of adhesive (548, 550) extends generally from proximal end (530) of buttress (522) to distal end (532) of buttress (522). First bead of adhesive (548) partially overlaps second bead of adhesive (550) along at least a portion of a length of buttress (522), specifically in the present example near proximal end (530) and near a middle area along the length of buttress (522) as shown in FIG. 11. In other areas, first bead of adhesive (548) is spaced apart from second bead of adhesive (550) along at least a portion of a length of buttress (522). Second bead of adhesive (550) extends further proximally compared to first bead of adhesive (548). Furthermore, first and second beads of adhesive (548, 550) extend distally to substantially the same extent relative to buttress (522). First bead of adhesive (548) is discontinuous near distal end (532) of buttress (522), where there is a space or gap (560) in first bead of adhesive (548). In contrast, second bead of adhesive (550) extends continuously from proximal end (530) to distal end (532) of buttress (522).

Now considering adhesive (520) as applied to second edge region (536), adhesive (520) comprises a third bead (552) and a fourth bead (554). Each bead of adhesive (552, 554) extends generally from proximal end (530) of buttress (522) to distal end (532) of buttress (522). Third bead of adhesive (552) partially overlaps fourth bead of adhesive (554) along at least a portion of a length of buttress (522), specifically in the present example near distal end (532) and near a middle area along the length of buttress (522). In other areas, third bead of adhesive (552) is spaced apart from fourth bead of adhesive (554) along at least a portion of a length of buttress (522). Fourth bead of adhesive (554) extends further proximally compared to third bead of adhesive (552). Furthermore, third and fourth beads of adhesive (552, 554) extend distally to substantially the same extent relative to buttress (522). In the present example, while third and fourth beads of adhesive (552, 554) have different shapes or patterns, both extend continuously from proximal end (530) to distal end (532) of buttress (522).

As mentioned above, first and second beads of adhesive (548, 550) are collectively asymmetrical with third and fourth beads of adhesive (552, 554) about longitudinal axis (A2) and lateral axis (A3). As also mentioned above, buttress (522) is configured to be cut into two halves about a longitudinal centerline of buttress (522). A first half of cut buttress (522) would include first edge region (534) and about half of center region (538), while a second half of cut buttress (522) would include second edge region (536) and about the other half of center region (538).

Considering now adhesive (520) as applied at proximal and distal ends (530, 532) of respective halves of buttress (522), in the present example, an uneven distribution of adhesive (520) is used. With respect to the first half of a cut buttress (522), there is more adhesive (520) at proximal end (530) of buttress (522) than at distal end (532) of buttress (522). However, with respect to the second half of a cut buttress (522), there is more adhesive (520) at distal end (532) of buttress (522) than at proximal end (530) of buttress (522). Referring to FIG. 11, these differences in adhesive (520) amounts are shown by circled regions, where first regions (R1) have more adhesive (520) than second regions (R2).

When using two buttress assemblies (516), when applied to end effector (40), each buttress assembly (516) is oriented opposite the other with first surfaces (526) containing adhesive (520) facing away from each other. In this arrangement, first edge region (534) of buttress assembly (516) attached with anvil (60) will be above and aligned with second edge region (536) of buttress assembly (516) attached with staple cartridge (70). Similarly, second edge region (536) of buttress assembly (516) attached with anvil (60) will be above and aligned with first edge region (534) of buttress assembly (516) attached with staple cartridge (70). In this arrangement, first regions (R1) having more adhesive (520) will be oriented opposite and aligned with second regions (R2) having less adhesive (520). By way of example only, at proximal end (530), buttress assembly (516) attached with anvil (60) will have first region (R1) positioned opposite and aligned with second region (R2) of the other buttress assembly (516) that is attached with staple cartridge (70). Likewise, and still at proximal end (530), buttress assembly (516) attached with anvil (60) will have second region (R2) positioned opposite and aligned with first region (R1) of the other buttress assembly (516) that is attached with staple cartridge (70). At distal end (532), buttress assembly (516) attached with anvil (60) will have second region (R2) positioned opposite and aligned with first region (R1) of the other buttress assembly (516) that is attached with staple cartridge (70). Likewise, and still at distal end (532), buttress assembly (516) attached with anvil (60) will have first region (R1) positioned opposite and aligned with second region (R2) of the other buttress assembly (516) that is attached with staple cartridge (70).

When considering buttress assembly (516) before it is cut in halves, there are two first regions (R1) in the present example for buttress assembly (516) attached on anvil (60) side of end effector (40). One such first region (R1) is within first edge region (534) at proximal end (530), and the other is within second edge region (536) at distal end (532). This is the same with respect to buttress assembly (516) attached on staple cartridge (70) side of end effector (40). These first regions (R1) with the more adhesive help buttresses (522) stay attached and aligned to and with the respective parts of end effector (40) when aggressively manipulating end effector (40), i.e. when piercing through ostomies, sliding axially onto tissue, etc. Furthermore, because buttress assemblies (516) are not yet cut, these areas of greater adhesive work to attach and retain the entire buttress assembly (516) with its respective parts of end effector (40).

Still considering buttress assembly (516) before it is cut in halves, there are two second regions (R2) in the present example for buttress assembly (516) attached on anvil (60) side of end effector (40). One such second region (R2) is within first edge region (534) at proximal end (530), and the other is within second edge region (536) at distal end (532). This is the same with respect to buttress assembly (516) attached on staple cartridge (70) side of end effector (40). These second regions (R2) with the less adhesive help buttresses (522) properly release from end effector (40) after a cut and staple operation. However, because buttress assemblies (516) are not yet cut, these areas of lower adhesive are still attached and retained on their respective parts of end effector (40) in part due to those first regions (R1) with greater adhesive (520) as discussed above.

Figure 12:
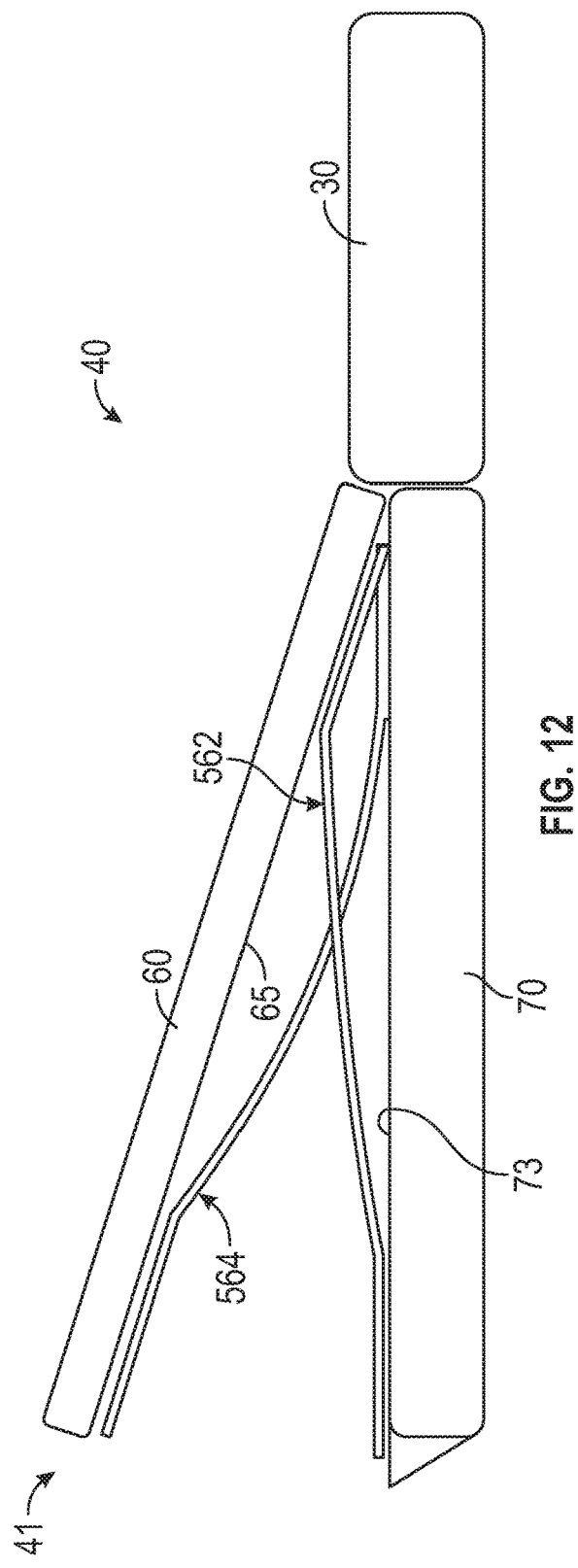
FIG. 12 depicts a side elevation view of an end effector for a surgical stapler in an open position, showing the buttress assembly of FIG. 11 releasing from the jaws of the end effector.

Referring to FIG. 12, a side view of end effector (40) is shown during an exemplary opening operation after a cut and staple action, and thus after buttress assembly (516) has been cut into halves. With the asymmetric distribution of adhesive (520) described above, when end effector (40) is opened after cutting and stapling, having first regions (R1) with more adhesive (520) opposite second regions (R2) with less adhesive (520) reduces the adhesive attachment to the respective surfaces on anvil (60) and staple cartridge (70). For instance, upon opening end effector (40) after a cutting and stapling action, second regions (R2) with less adhesive (520) detach or release from end effector (40) prior to first regions (R1) with the greater adhesive (520). As mentioned above, prior to cutting buttress assembly (516) into halves, buttress assembly (516) operates as a unit and thus the combined first areas (R1) with greater adhesive provide for attachment and retention of buttress assembly (516). However, this changes once buttress assembly (516) is cut into halves as second regions (R2) will now release from end effector (40).

For ease of illustration, FIG. 12 shows end effector (40) loaded with a single buttress assembly (516) on staple cartridge (70) side, where a cut and staple operation has occurred such that the knife of end effector (40) has cut buttress assembly (516) into halves. In FIG. 12, first half (562) and second half (564) of buttress assembly (516) are shown with their attachment and release profiles. First half (562) represents first edge region (534) and half of center region (538) as illustrated in FIG. 11. As shown, first half (562) has first region (R1) with the greater adhesive (520) located at the proximal end of staple cartridge (70). Thus when opening end effector (40) initially, first half (562) remains attached with staple cartridge (70) near the proximal end of staple cartridge (70). First half (562) has second region (R2) with less adhesive (520) located at the distal end of staple cartridge (70). Thus when opening end effector (40) initially, first half (562) releases from staple cartridge (70) near the distal end of staple cartridge (70). Second half (564) represents second edge region (536) and half of center region (538) as illustrated in FIG. 11. As shown, second half (564) has first region (R1) with the greater adhesive (520) located at the distal end of staple cartridge (70). Thus when opening end effector (40) initially, second half (564) remains attached with staple cartridge (70) near the distal end of staple cartridge (70). Second half (564) has second region (R2) with less adhesive (520) located at the proximal end of staple cartridge (70). Thus when opening end effector (40) initially, second half (564) releases from staple cartridge (70) near the proximal end of staple cartridge (70). This pattern of attachment and release post cutting and stapling would also be evident on anvil (60) side of end effector (40) for buttress assembly (516) loaded onto anvil (60).

Other than the disparity in adhesive (520) described above, another factor that contributes to the release of buttress assembly (516) from end effector (40) is the large aperture or large motion of distal end (41) of end effector (40) when being opened after a cut and staple action. This large range of motion for distal end (41) of end effector (40) also works with the fact that after the cut and staple action two opposing halves of two buttress assemblies (516) are now stapled together with tissue therebetween. Accordingly, these factors provide for release of buttress assemblies (516) even at first regions (R1) that have greater adhesive that was adhering buttress assemblies (516) to respective parts of end effector (40).

Referring now to FIGS. 13 and 14, FIG. 13 illustrates a buttress assembly (616) having another exemplary asymmetric adhesive distribution. Buttress assembly (616) is configured similar to buttress assemblies (316, 318) described above, except with a different adhesive application pattern. Accordingly, two buttress assemblies (616) can be used in place of buttress assemblies (316, 318) described above. This includes being used in place of buttress assemblies (316, 318) with applicator (300) and end effector (40).

In the present example of FIG. 13, buttress assembly (616) comprises buttress (622) and adhesive (620) on one side of buttress (622). Buttress (622) comprises a first surface (626) and a second surface opposite to first surface (626). Buttress also includes a proximal end (630) and a distal end (632). As with buttress assemblies (316, 318) when buttress assembly (616) is attached with end effector (40) distal end (632) of buttress (622) aligns with a distal end (41) of end effector (40). With this configuration, buttress (622) defines a length extending from proximal end (630) to distal end (632). Buttress (622) further defines a longitudinal axis (A4) that extends between proximal end (630) and distal end (632). Buttress (622) includes a first edge region (634), a second edge region (636), and a center region (638) between and separating first edge region (634) and second edge region (636). Buttress (622) defines a width extending orthogonal to its length as defined above, where its width extends from first edge region (634) across center region (638) and through second edge region (636).

In the present example, adhesive (620) is applied onto first surface (626) of buttress (622). Adhesive (620) extends from proximal end (630) to distal end (632) of buttress (622). Moreover, in the present example, at least a portion of adhesive (620) extends continuously or in an uninterrupted manner. Adhesive (620) is located along first edge region (634) and second edge region (636), with center region (638) being substantially free of adhesive (620). As described above, adhesive (620) is applied to buttress in a manner such that adhesive (620) comprises a height such that adhesive (620) is proud of buttress (622). The height of adhesive (620) is configured to facilitate adhesive (620) making good contact with either underside (65) of anvil (60) of end effector (40) or deck (73) of staple cartridge (70) of end effector (40) depending on the orientation of end effector (40) when loading buttress assembly (616) onto end effector (40) using applicator (300).

The continuous nature of adhesive (620) along with the height of adhesive (620) act to seal the edges of buttress (622) to the part of end effector (40) to which buttress (622) attaches. With this sealing attachment, in use the amount of moisture that can reach buttress assembly (616) is reduced. By controlling moisture migration in this manner, buttress assembly (616) can have longer attachment times with end effector (40). This can give users greater lengths of time to position and manipulate end effector (40) before executing a cutting and stapling action, thereby applying buttresses (622) as reinforcing structures to the cut and stapled site.

Referring still to FIG. 13, center region (638) of buttress (622) comprises slits (640), which are structurally and functionally the same as slits (340) of buttress assemblies (316, 318). In the illustrated version, slits (640) include a proximal slit (642), a distal slit (644), and an intermediate slit (646) between proximal and distal slits (642, 644). In the present example, longitudinal axis (A4) passes through slits (640), and on each side of center region (638), adhesive (620) defines a pattern that is asymmetrical with the other side about longitudinal axis (A4). Adhesive (620) is further asymmetrical about a lateral axis (A5) that extends orthogonal relative to longitudinal axis (A4) through a midpoint of buttress assembly (616) as measured between proximal and distal ends (630, 632).

Now considering adhesive (620) as applied to first edge region (634), adhesive (620) comprises a first bead (648) and a second bead (650). Each bead of adhesive (648, 650) extends generally from proximal end (630) of buttress (622) to distal end (632) of buttress (622). First bead of adhesive (648) partially overlaps second bead of adhesive (650) along at least a portion of a length of buttress (622), specifically in the present example near proximal end (630), near a middle area along the length of buttress (622), and near distal end (632) as shown in FIG. 13. In other areas, first bead of adhesive (648) is spaced apart from second bead of adhesive (650) along at least a portion of a length of buttress (622). Second bead of adhesive (650) extends further proximally compared to first bead of adhesive (648). Furthermore, first and second beads of adhesive (648, 650) extend distally to substantially the same extent relative to buttress (622). In the present example, while first and second beads of adhesive (648, 650) have different shapes or patterns, both extend continuously from proximal end (630) to distal end (632) of buttress (622).

Now considering adhesive (620) as applied to second edge region (636), adhesive (620) comprises a third bead (652) and a fourth bead (654). Each bead of adhesive (652, 654) extends generally from proximal end (630) of buttress (622) to distal end (632) of buttress (622). Third bead of adhesive (652) partially overlaps fourth bead of adhesive (654) along at least a portion of a length of buttress (622), specifically in the present example near distal end (632) and near proximal end (630). In other areas, third bead of adhesive (652) is spaced apart from fourth bead of adhesive (654) along at least a portion of a length of buttress (622). Fourth bead of adhesive (654) extends further proximally compared to third bead of adhesive (652). Furthermore, third and fourth beads of adhesive (652, 654) extend distally to substantially the same extent relative to buttress (622). Third bead of adhesive (652) is discontinuous near a middle section of buttress (622), where there is a space or gap (660) in third bead of adhesive (652). In contrast, fourth bead of adhesive (654) extends continuously from proximal end (630) to distal end (632) of buttress (622).

As mentioned above, first and second beads of adhesive (648, 650) are collectively asymmetrical with third and fourth beads of adhesive (652, 654) about longitudinal axis (A4) and lateral axis (A5). As also mentioned above, buttress (622) is configured to be cut into two halves about a longitudinal centerline of buttress (622). A first half of cut buttress (622) would include first edge region (634) and about half of center region (638), while a second half of cut buttress (622) would include second edge region (636) and about the other half of center region (638).

Considering now adhesive (620) as applied at proximal and distal ends (630, 632) of respective halves of buttress (622), in the present example, an uneven distribution of adhesive (620) is used. With respect to the first half of a cut buttress (622), there is more adhesive (620) at a middle region of buttress (622) than at proximal and distal ends (630, 632) of buttress (622). However, with respect to the second half of a cut buttress (622), there is more adhesive (620) at proximal and distal ends (630, 632) of buttress (522) than at the middle region of buttress (622). Referring to FIG. 13, these differences in adhesive (620) amounts are shown by circled regions, where first regions (R1) have more adhesive (620) than second regions (R2).

When using two buttress assemblies (616), when applied to end effector (40), each buttress assembly (616) is oriented opposite the other with first surfaces (626) containing adhesive (620) facing away from each other. In this arrangement, first edge region (634) of buttress assembly (616) attached with anvil (60) will be above and aligned with second edge region (636) of buttress assembly (616) attached with staple cartridge (70). Similarly, second edge region (636) of buttress assembly (616) attached with anvil (60) will be above and aligned with first edge region (634) of buttress assembly (616) attached with staple cartridge (70). In this arrangement, first regions (R1) having more adhesive (620) will be oriented opposite and aligned with second regions (R2) having less adhesive (620). By way of example only, at proximal end (630), buttress assembly (616) attached with anvil (60) will have first region (R1) positioned opposite and aligned with second region (R2) of the other buttress assembly (616) that is attached with staple cartridge (70). Likewise, and still at proximal end (630), buttress assembly (616) attached with anvil (60) will have second region (R2) positioned opposite and aligned with first region (R1) of the other buttress assembly (616) that is attached with staple cartridge (70). At distal end (632), buttress assembly (616) attached with anvil (60) will have second region (R2) positioned opposite and aligned with first region (R1) of the other buttress assembly (616) that is attached with staple cartridge (70). Likewise, and still at distal end (632), buttress assembly (616) attached with anvil (60) will have first region (R1) positioned opposite and aligned with second region (R2) of the other buttress assembly (616) that is attached with staple cartridge (70). Near the middle region, buttress assembly (616) attached with anvil (60) will have first region (R1) positioned opposite and aligned with second region (R2) of the other buttress assembly (616) that is attached with staple cartridge (70). Likewise, and still at the middle region, buttress assembly (616) attached with anvil (60) will have second region (R2) positioned opposite and aligned with first region (R1) of the other buttress assembly (616) that is attached with staple cartridge (70).

When considering buttress assembly (616) before it is cut in halves, there are three first regions (R1) in the present example for buttress assembly (616) attached on anvil (60) side of end effector (40). One such first region (R1) is within first edge region (634) at the middle region of buttress (622), another first region (R1) is within second edge region (636) at distal end (632), and another first region (R1) is also within second edge region (636) at proximal end (630). This is the same with respect to buttress assembly (616) attached on staple cartridge (70) side of end effector (40). These first regions (R1) with the more adhesive help buttresses (622) stay attached and aligned to and with the respective parts of end effector (40) when aggressively manipulating end effector (40), i.e. when piercing through ostomies, sliding axially onto tissue, etc. Furthermore, because buttress assemblies (616) are not yet cut, these areas of greater adhesive work to attach and retain the entire buttress assembly (616) with its respective parts of end effector (40).

Still considering buttress assembly (616) before it is cut in halves, there are three second regions (R2) in the present example for buttress assembly (616) attached on anvil (60) side of end effector (40). One such second region (R2) is within first edge region (634) at proximal end (630), another is within first edge region (634) at distal end (632), another is within second edge region (636) at the middle region of buttress (622). This is the same with respect to buttress assembly (616) attached on staple cartridge (70) side of end effector (40). These second regions (R2) with the less adhesive help buttresses (622) properly release from end effector (40) after a cut and staple operation. However, because buttress assemblies (616) are not yet cut, these areas of lower adhesive are still attached and retained on their respective parts of end effector (40) in part due to those first regions (R1) with greater adhesive (620) as discussed above.

Referring to FIG. 14, a side view of end effector (40) is shown during an exemplary opening operation after a cut and staple action, and thus after buttress assembly (616) has been cut into halves. With the asymmetric distribution of adhesive (620) described above, when end effector (40) is opened after cutting and stapling, having first regions (R1) with more adhesive (620) opposite second regions (R2) with less adhesive (620) reduces the adhesive attachment to the respective surfaces on anvil (60) and staple cartridge (70). For instance, upon opening end effector (40) after a cutting and stapling action, second regions (R2) with less adhesive (620) detach or release from end effector (40) prior to first regions (R1) with the greater adhesive (620). As mentioned above, prior to cutting buttress assembly (616) into halves, buttress assembly (616) operates as a unit and thus the combined first areas (R1) with greater adhesive provide for attachment and retention of buttress assembly (616). However, this changes once buttress assembly (616) is cut into halves as second regions (R2) will now release from end effector (40).

For ease of illustration, FIG. 14 shows end effector (40) loaded with a single buttress assembly (616) on staple cartridge (70) side, where a cut and staple operation has occurred such that the knife of end effector (40) has cut buttress assembly (616) into halves. In FIG. 14, first half (662) and second half (664) of buttress assembly (616) are shown with their attachment and release profiles. First half (662) represents first edge region (634) and half of center region (638) as illustrated in FIG. 13. As shown, first half (662) has first region (R1) with the greater adhesive (620) located at a middle region of staple cartridge (70). Thus when opening end effector (40) initially, first half (662) remains attached with staple cartridge (70) near the middle region of staple cartridge (70). First half (662) has second region (R2) with less adhesive (620) located at the proximal and distal ends of staple cartridge (70). Thus when opening end effector (40) initially, first half (662) releases from staple cartridge (70) near the proximal and distal ends of staple cartridge (70).

Second half (664) represents second edge region (636) and half of center region (638) as illustrated in FIG. 13. As shown, second half (664) has first region (R1) with the greater adhesive (620) located at the proximal and distal ends of staple cartridge (70). Thus when opening end effector (40) initially, second half (664) remains attached with staple cartridge (70) near the proximal and distal ends of staple cartridge (70). Second half (664) has second region (R2) with less adhesive (620) located at the middle region of staple cartridge (70). Thus when opening end effector (40) initially, second half (664) releases from staple cartridge (70) near the middle region of staple cartridge (70). This pattern of attachment and release post cutting and stapling would also be evident on anvil (60) side of end effector (40) for buttress assembly (616) loaded onto anvil (60).

Other than the disparity in adhesive (620) described above, another factor that contributes to the release of buttress assembly (616) from end effector (40) is the large aperture or large motion of distal end (41) of end effector (40) when being opened after a cut and staple action. This large range of motion for distal end (41) of end effector (40) also works with the fact that after the cut and staple action two opposing halves of two buttress assemblies (616) are now stapled together with tissue therebetween. Accordingly, these factors provide for release of buttress assemblies (616) even at first regions (R1) that have greater adhesive that was adhering buttress assemblies (616) to respective parts of end effector (40).

As shown and described in the examples above, using an asymmetric distribution of adhesive (520, 620) on buttress assemblies (516, 616) allows for a reduction in the release force, or force required to release buttress assemblies (516, 616) from end effector (40) after buttress assemblies (516, 616) are cut into halves. This allows for buttress assemblies (516, 616) to be configured with a controlled release where certain portions of buttress assemblies (516, 616) are configured to release earlier or sooner than other portions.

Furthermore, strategically locating regions of asymmetric adhesive distribution provides for adequate attachment and retention of one cut buttress assemblies (516, 616). While multiple adhesive distributions have been shown and described herein, other adhesive distributions can be used to achieve desired attachment, retention, and release properties for buttress assemblies described herein. In view of the teachings herein, such other patterns of adhesive distribution for buttress assemblies described herein will be apparent to those of ordinary skill in the art.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A buttress assembly for reinforcing tissue layers joined by surgical stapling, comprises (a) a buttress comprising a first surface and a second surface, wherein the buttress further comprises a proximal end and a distal end. The buttress defines a longitudinal axis extending between the proximal end and the distal end, wherein the buttress further comprises a center region adjacent to a first edge region on one side of the center region and adjacent to a second edge region on the other side of the center region. The buttress assembly also comprises (b) an adhesive applied to a select one of the first surface and the second surface of the buttress, wherein the adhesive extends continuously from the proximal end of the buttress to the distal end of the buttress. The adhesive is located along the first edge region and the second edge region leaving the center region of the buttress substantially free of the adhesive.

Example 2

The buttress assembly of Example 1, wherein the center region of the buttress comprises one or more slits configured to promote separation of the buttress into halves.

Example 3

The buttress assembly of any one or more of Examples 1 through 2, wherein the adhesive comprises an uneven distribution that comprises more of the adhesive at the distal end of the buttress than at the proximal end of the buttress.

Example 4

The buttress assembly of any one or more of Examples 1 through 3, wherein the adhesive comprises a first bead of the adhesive extending from the proximal end of the buttress to the distal end of the buttress, and wherein the adhesive further comprises a second bead of the adhesive extending from the proximal end of the buttress to the distal end of the buttress.

Example 5

The buttress assembly of Example 4, wherein the first bead of the adhesive partially overlaps the second bead of the adhesive along at least a portion of a length of the buttress.

Example 6

The buttress assembly of any one or more of Examples 4 through 5, wherein the first bead of the adhesive is spaced apart from the second bead of the adhesive along at least a portion of the length of the buttress.

Example 7

The buttress assembly of any one or more of Examples 4 through 6, wherein the second bead of the adhesive extends further proximally than the first bead of the adhesive.

Example 8

The buttress assembly of any one or more of Examples 4 through 7, wherein the first bead of the adhesive and the second bead of the adhesive extend distally to substantially the same extent relative to the buttress.

Example 9

The buttress assembly of any one or more of Examples 4 through 8, wherein the adhesive comprises a third bead of the adhesive extending from the proximal end of the buttress to the distal end of the buttress, and wherein the adhesive further comprises a fourth bead of the adhesive extending from the proximal end of the buttress to the distal end of the buttress.

Example 10

The buttress assembly of any one or more of Examples 4 through 9, wherein the first and the second beads of the adhesive are collectively symmetrical with the third and the fourth beads of the adhesive about the longitudinal axis of the buttress that defines a centerline of the buttress.

Example 11

The buttress assembly of any one or more of Examples 1 through 10, wherein the adhesive comprises a minimum height such that where the adhesive is applied to the buttress the adhesive sits proud of the buttress.

Example 12

The buttress assembly of Example 11, wherein the minimum height of the adhesive is between about 0.254 mm and about 1.27 mm.

Example 13

The buttress assembly of any one or more of Examples 11 through 12, wherein the minimum height of the adhesive is between about 0.4064 mm and about 0.762 mm.

Example 14

The buttress assembly of any one or more of Examples 11 through 13, wherein the minimum height of the adhesive is configured to substantially match a depth of a staple forming pocket of an anvil of an end effector of a surgical stapler.

Example 15

The buttress assembly of any one or more of Examples 11 through 14, wherein the minimum height of the adhesive is configured to substantially match a height of a pocket extender of a staple cartridge of an end effector of a surgical stapler.

Example 16

A buttress assembly for reinforcing tissue layers joined by surgical stapling, comprises (a) a buttress comprising a first surface and a second surface, wherein the buttress further comprises a proximal end and a distal end. The buttress defines a length from the proximal end to the distal end, wherein the buttress defines a longitudinal axis extending between the proximal end and the distal end. The buttress further comprises a center region adjacent to a first edge region on one side of the center region and adjacent to a second edge region on the other side of the center region, wherein the buttress is configured to be cut into substantially equal halves by cutting through the center region. The buttress assembly also comprises (b) an adhesive applied to a select one of the first surface and the second surface of the buttress, wherein the adhesive extends from the proximal end of the buttress to the distal end of the buttress. The adhesive is located along the first edge region and the second edge region leaving the center region of the buttress substantially free of the adhesive, wherein the adhesive comprises an asymmetric distribution along the length of the buttress.

Example 17

The buttress assembly of Example 16, wherein the adhesive on the first edge region and the second edge region changes between areas of greater adhesive and areas of lesser adhesive along the length of the buttress, wherein the areas of greater adhesive on the first edge region are located opposite to the areas of lesser adhesive on the second edge region, and wherein the areas of greater adhesive on the second edge region are located opposite to the areas of lesser adhesive on the first edge region.

Example 18

The buttress assembly of any one or more of Examples 16 through 17, wherein the asymmetric distribution of the adhesive is configured to reduce the force needed for releasing the buttress assembly from a select one of an anvil and a staple cartridge of an end effector of a surgical stapler when opening the end effector.

Example 19

An apparatus for reinforcing tissue layers joined by surgical stapling, comprises (a) a pair of buttress assemblies, each buttress assembly of the pair comprising (i) a buttress comprising a first surface and a second surface, wherein the buttress further comprises a proximal end and a distal end, wherein the buttress defines a length from the proximal end to the distal end, wherein the buttress further comprises a center region adjacent to a first edge region on one side of the center region and adjacent to a second edge region on the other side of the center region, wherein the buttress is configured to be cut into substantially equal halves by cutting through the center region, and (ii) an adhesive applied to a select one of the first surface and the second surface of the buttress, wherein the adhesive extends from the proximal end of the buttress to the distal end of the buttress, wherein the adhesive is located along the first edge region and the second edge region leaving the center region of the buttress substantially free of the adhesive, wherein the adhesive comprises an asymmetric distribution along the length of the buttress having the adhesive on the first edge region and the second edge region changing between areas of greater adhesive and areas of lesser adhesive, wherein the areas of greater adhesive on the first edge region are located opposite to the areas of lesser adhesive on the second edge region, and wherein the areas of greater adhesive on the second edge region are located opposite to the areas of lesser adhesive on the first edge region. The apparatus also comprises (b) each of the buttress assemblies are configured to be positioned in an opposing manner with the adhesive of one of the buttress assemblies facing away from the adhesive of the other of the buttress assemblies, wherein when positioned in the opposing manner, the areas of greater adhesive on one of the buttress assemblies are aligned with the areas of lesser adhesive on the other of the buttress assemblies.

Example 20

The apparatus of Example 19, wherein the center region of the buttress comprises one or more slits configured to promote cutting the buttress into halves.

V. Miscellaneous

While the terms "buttress" and "buttress assembly" are used throughout this disclosure, it should be understood that the term is not intended to limit the scope of the present invention in any way. For instance, use of the terms "buttress" and "buttress assembly" is not intended to demonstrate contemplation that a "buttress" or "buttress assembly" can only be used to provide structural support to a staple line or serve any other particular purpose. It is contemplated that "buttress" or "buttress assembly" may serve a variety of purposes in addition to or as an alternative to providing structural support to a staple line. The terms "buttress" and "buttress assembly" should therefore be read broadly to include any kind of adjunct to a staple line that serves any suitable purpose.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

In addition to the foregoing, it should also be understood that any of the various buttress assemblies described herein may be further constructed and operable in accordance with at least some of the teachings of U.S. Pat. Pub. No. 2016/0278774, entitled "Method of Applying a Buttress to a Surgical Stapler," published Sep. 29, 2016, issued as U.S. Pat. No. 10,349,939 on Jul. 16, 2019, the disclosure of which is incorporated by reference herein; U.S. Pat. Pub. No. 2017/0049444, entitled "Implantable Layers for a Surgical Instrument," published Feb. 23, 2017, issued as U.S. Pat. No. 10,835,249 on Nov. 17, 2020, the disclosure of which is incorporated by reference herein; U.S. Pat. Pub. No. 2017/0086837, entitled "Compressible Adjunct with Crossing Spacer Fibers," published Mar. 30, 2017, issued as U.S. Pat. No. 10,433,846 on Oct. 8,2019, the disclosure of which is incorporated by reference herein; and U.S. Pat. Pub. No. 2017/0086842, entitled "Method for Applying an Implantable Layer to a Fastener Cartridge," published Mar. 30, 2017, the disclosure of which is incorporated by reference herein. Furthermore, in addition to the methods described herein, any of the various buttress assemblies described herein may be applied to end effector (40) in accordance with at least some of the teachings of U.S. Pat. Pub. No. 2017/0056016, entitled "Surgical Stapler Buttress Applicator with End Effector Actuated Release Mechanism," published Mar. 2, 2017, issued as U.S. Pat. No. 10,342,542 on Jul. 9, 2019, the disclosure of which is incorporated by reference herein; U.S. Pat. Pub. No. 2017/0056017, entitled "Surgical Stapler Buttress Applicator with Multi-Zone Platform for Pressure Focused Release," published Mar. 2, 2017, issued as U.S. Pat. No. 10,639,039 on May 5, 2020, the disclosure of which is incorporated by reference herein; U.S. Pat. Pub. No. 2017/0055980, entitled "Surgical Stapler Buttress Applicator with Spent Staple Cartridge Lockout," published Mar. 2, 2017, the disclosure of which is incorporated by reference herein; U.S. Pat. Pub. No. 2017/0056018, entitled "Surgical Stapler Buttress Applicator with State Indicator," published Mar. 2, 2017, issued as U.S. Pat. No. 10,349,940 on Jul. 16, 2019, the disclosure of which is incorporated by reference herein; U.S. Pat. Pub. No. 2017/0055982, entitled "Surgical Stapler Buttress Applicator with Multi-Point Actuated Release Mechanism," published Mar. 2, 2017, issued as U.S. Pat. No. 10,342,532 on Jul. 9,2019, the disclosure of which is incorporated by reference herein; U.S. Pat. Pub. No. 2017/0055981, entitled "Method of Applying a Buttress to a Surgical Stapler End Effector," published Mar. 2, 2017, issued as U.S. Pat. No. 10,166,023 on Jan. 1, 2019, the disclosure of which is incorporated by reference herein; and/or U.S. Pat. Pub. No. 2017/0086842, entitled "Method for Applying an Implantable Layer to a Fastener Cartridge," published Mar. 30, 2017, the disclosure of which is incorporated by reference herein. Various suitable ways in which the teachings herein may be combined with various teachings of the above-cited references will be apparent to those of ordinary skill in the art.

It should also be understood that the teachings herein may be readily combined with various teachings in U.S. patent application No. 16/235,488, entitled "Configuration of Buttress for Surgical Stapler," filed on Dec. 28, 2018, published as U.S. Pub. No. 2020/0205821 on Jul. 2, 2020, the disclosure of which is incorporated by reference herein. Various suitable ways in which the teachings herein may be combined with the teachings of U.S. patent application No. 16/235,488, filed on Dec. 28, 2018, published us U.S Pub. No. 2020/0205821 on Jul. 2, 2020, will be apparent to those of ordinary skill in the art.

It should also be understood that the teachings herein may be readily combined with various teachings in U.S. patent application No. 16/235,503, entitled "Surgical Stapler Buttress with Tissue In-Growth Promotion," filed on Dec. 28, 2018, published on U.S. Pub. No. 2020/0205822 on Jul. 2, 2020, the disclosure of which is incorporated by reference herein. Various suitable ways in which the teachings herein may be combined with the teachings of U.S. patent application No. 16/235,503, filed on Dec. 28, 2018, published on U.S. Pub. No. 2020/0205822 on Jul. 2, 2020, will be apparent to those of ordinary skill in the art.

It should also be understood that the teachings herein may be readily combined with various teachings in U.S. patent application No. 16/235,522, entitled "Applicator for Surgical Stapler Buttress," filed on Dec. 28, 2018, published as U.S. Pub No. 2020/0205823 on Jul. 2, 2020, the disclosure of which is incorporated by reference herein. Various suitable ways in which the teachings herein may be combined with the teachings of U.S. patent application Ser. No. 16/235,522, filed on Dec. 28, 2018, published as U.S. Pub. No. 2020/0205823 on Jul. 2, 2020, will be apparent to those of ordinary skill in the art.

It should also be understood that the teachings herein may be readily combined with various teachings in U.S. patent application No. 15/235,541, entitled "Packaging for Surgical Stapler Buttress," filed on Dec. 28, 2018, published as U.S. Pub. No. 2020/0205824 on Jul. 2, 2020, the disclosure of which is incorporated by reference herein. Various suitable ways in which the teachings herein may be combined with the teachings of U.S. patent application Ser. No. 15/235,541, filed on Dec. 28, 2018, published as U.S. Pub. No. 2020/0205824 on Jul. 2, 2020, will be apparent to those of ordinary skill in the art.

It should also be understood that the teachings herein may be readily combined with various teachings in U.S. patent application No. 29/675,168, entitled "Applicator for Surgical Stapler Buttress," filed on Dec. 28, 2018, issued as U.S. Pat. No. D901,686 on Nov. 10, 2020, the disclosure of which is incorporated by reference herein. Various suitable ways in which the teachings herein may be combined with the teachings of U.S. patent application Ser. No. 29/675,168, filed on Dec. 28, 2018, issued as U.S. Pat. No. D901,686 on Nov. 10, 2020, will be apparent to those of ordinary skill in the art.

It should also be understood that the teachings herein may be readily combined with various teachings in U.S. patent application No. 29/695,170, entitled "Buttress for Surgical Stapler," filed on Dec. 28, 2018, the disclosure of which is incorporated by reference herein. Various suitable ways in which the teachings herein may be combined with the teachings of U.S. patent application Ser. No. 29/695,170, filed on Dec. 28, 2018, will be apparent to those of ordinary skill in the art.

It should also be understood that the teachings herein may be readily combined with various teachings in U.S. patent application No. 29/675,172, entitled "Tray for Surgical Stapler Buttress Applicator," filed on Dec. 28, 2018, the disclosure of which is incorporated by reference herein. Various suitable ways in which the teachings herein may be combined with the teachings of U.S. patent application No. 29/675,172, filed on Dec. 28, 2018, will be apparent to those of ordinary skill in the art.

It should also be understood that the teachings herein may be readily combined with various teachings in U.S. patent application No. 16/235,617, entitled "Method of Applying Buttresses to Surgically Cut and Stapled Sites," filed on Dec. 28, 2018, published as U.S. Pub. No. 2020/0205825 on Jul. 2, 2020; the disclosure of which is incorporated by reference herein. Various suitable ways in which the teachings herein may be combined with the teachings of U.S. patent application No. 16/235,617, filed on Dec. 28, 2018, published as U.S. Pub. No. 2020/0205825 on Jul. 2, 2020, will be apparent to those of ordinary skill in the art.

It should also be understood that the teachings herein may be readily combined with various teachings in U.S. patent application No. 16/235,630, entitled "Curved Tip Surgical Stapler Buttress Assembly Applicator with Opening Feature for Curved Tip Alignment," filed on Dec. 28. 2018, published as U.S. Pub No. 2020/0205826 on Jul. 2, 2020; the disclosure of which is incorporated by reference herein. Various suitable ways in which the teachings herein may be combined with the teachings of U.S. patent application No. 16/235,630, filed on Dec. 28, 2018 published as U.S. Pub. No. 2020/0205826 on Jul. 2, 2020, will be apparent to those of ordinary skill in the art.

It should also be understood that the teachings herein may be readily combined with various teachings in U.S. patent application No. 16/235,670, entitled "Curved Tip Surgical Stapler Buttress Assembly Applicator with Proximal Alignment Features," filed on Dec. 28, 2018, issued as U.S. Pat. No. 10,905,424 on Feb. 2, 2021; the disclosure of which is incorporated by reference herein. Various suitable ways in which the teachings herein may be combined with the teachings of U.S. patent application No. 16/235,670, filed on Dec. 28, 2018, issued as U.S. Pat. No. 10,905,424 on Feb. 2, 2021, will be apparent to those of ordinary skill in the art.

It should also be understood that the teachings herein may be readily combined with various teachings in U.S. patent application No. 16/235,681, entitled "Curved Tip Surgical Stapler Buttress Assembly Applicator with Compression Layer Pocket Feature," filed on Dec. 28, 2018, published as U.S. Pub. No. 2020/0205807 on Jul. 2, 2020; the disclosure of which is incorporated by reference herein. Various suitable ways in which the teachings herein may be combined with the teachings of U.S. patent application No. 16/235, 681, filed on Dec. 28, 2018, published as U.S. Pub. No. 2020/0205807 on Jul. 2, 2020, will be apparent to those of ordinary skill in the art.

It should also be understood that the teachings herein may be readily combined with various teachings in U.S. patent application No. 29/675,197, entitled "Applicator for a Surgical Stapler Buttress," filed on Dec. 28, 2018, issued as U.S. Pat. No. D903,115 ono Nov. 24, 2020; the disclosure of which is incorporated by reference herein. Various suitable ways in which the teachings herein may be combined with the teachings of U.S. patent application No. 29/675,197, filed on Dec. 28, 2018, issued as U.S. Pat. No. D903,115 on Nov. 24, 2020, will be apparent to those of ordinary skill in the art.

It should also be understood that the teachings herein may be readily combined with various teachings in U.S. patent application No. 29/675,199, entitled "Buttress Assembly for a Surgical Stapler," filed on Dec. 28, 2018; the disclosure of which is incorporated by reference herein. Various suitable ways in which the teachings herein may be combined with the teachings of U.S. patent application No. 29/675,199, filed on Dec. 28, 2018, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A buttress assembly for reinforcing tissue layers joined by surgical stapling, wherein the buttress assembly comprises:
   (a) a buttress comprising a first surface and a second surface, wherein the buttress further comprises a proximal end and a distal end, wherein the buttress defines a longitudinal axis extending between the proximal end and the distal end, wherein the buttress further comprises a center region adjacent to a first edge region on one side of the center region and adjacent to a second edge region on the other side of the center region; and
   (b) an adhesive applied to a select one of the first surface and the second surface of the buttress, wherein the adhesive extends continuously from the proximal end of the buttress to the distal end of the buttress, wherein the adhesive is located along the first edge region and the second edge region leaving the center region of the buttress substantially free of the adhesive, wherein the adhesive includes first and second beads that extend from the proximal end of the buttress to the distal end of the buttress, wherein the first bead partially overlaps the second bead along at a portion of a length of the buttress.

2. The buttress assembly of claim 1, wherein the center region of the buttress comprises one or more slits configured to promote separation of the buttress into halves.

3. The buttress assembly of claim 2, further comprising a gap at the distal end of the buttress that aligns with the center region, wherein a slit of the one or more slits extends proximally from the gap.

4. The buttress assembly of claim 1, wherein the adhesive comprises an uneven distribution that comprises more of the adhesive at the distal end of the buttress than at the proximal end of the buttress.

5. The buttress assembly of claim 1, wherein the first bead of the adhesive is spaced apart from the second bead of the adhesive along at least a portion of the length of the buttress.

6. The buttress assembly of claim 1, wherein the second bead of the adhesive extends further proximally than the first bead of the adhesive.

7. The buttress assembly of claim 1, wherein the first bead of the adhesive and the second bead of the adhesive extend distally to substantially the same extent relative to the buttress.

8. The buttress assembly of claim 1, wherein the adhesive comprises a third bead of the adhesive extending from the proximal end of the buttress to the distal end of the buttress, and wherein the adhesive further comprises a fourth bead of the adhesive extending from the proximal end of the buttress to the distal end of the buttress.

9. The buttress assembly of claim 8, wherein the first and the second beads of the adhesive are collectively symmetrical with the third and the fourth beads of the adhesive about the longitudinal axis of the buttress that defines a centerline of the buttress.

10. The buttress assembly of claim 8, wherein the third bead at least partially overlaps the fourth bead along at least a portion of a length of the buttress.

11. The buttress assembly of claim 1, wherein the adhesive comprises a minimum height such that where the adhesive is applied to the buttress the adhesive sits proud of the buttress.

12. The buttress assembly of claim 11, wherein the minimum height of the adhesive is between about 0.254 mm and about 1.27 mm.

13. The buttress assembly of claim 11, wherein the minimum height of the adhesive is between about 0.4064 mm and about 0.762 mm.

14. The buttress assembly of claim 11, wherein the minimum height of the adhesive is configured to substantially match a depth of a staple forming pocket of an anvil of an end effector of a surgical stapler.

15. The buttress assembly of claim 11, wherein the minimum height of the adhesive is configured to substantially match a height of a pocket extender of a staple cartridge of an end effector of a surgical stapler.

16. A buttress assembly for reinforcing tissue layers joined by surgical stapling, wherein the buttress assembly comprises:
   (a) a buttress comprising a first surface and a second surface, wherein the buttress further comprises a proximal end and a distal end, wherein the buttress defines a length from the proximal end to the distal end, wherein the buttress defines a longitudinal axis extending between the proximal end and the distal end, wherein the buttress further comprises a center region adjacent to a first edge region on one side of the center region and adjacent to a second edge region on the other side of the center region, wherein the buttress is configured to be cut into substantially equal halves by cutting through the center region; and
   (b) an adhesive applied to a select one of the first surface and the second surface of the buttress, wherein the adhesive extends from the proximal end of the buttress to the distal end of the buttress, wherein the adhesive is located along the first edge region and the second edge region leaving the center region of the buttress substantially free of the adhesive, wherein the adhesive includes a portion of adhesive that extends continuously from the proximal end of the buttress to the distal end of the buttress and comprises an asymmetric distribution along the length of the buttress.

17. The buttress assembly of claim 16, wherein the adhesive on the first edge region and the second edge region changes between areas of greater adhesive and areas of lesser adhesive along the length of the buttress, wherein the areas of greater adhesive on the first edge region are located opposite to the areas of lesser adhesive on the second edge region, and wherein the areas of greater adhesive on the second edge region are located opposite to the areas of lesser adhesive on the first edge region.

18. The buttress assembly of claim 16, wherein the asymmetric distribution of the adhesive is configured to reduce the force needed for releasing the buttress assembly from a select one of an anvil and a staple cartridge of an end effector of a surgical stapler when opening the end effector.

19. An apparatus for reinforcing tissue layers joined by surgical stapling, wherein the apparatus comprises:
   (a) a pair of buttress assemblies, each buttress assembly of the pair comprising:
      (i) a buttress comprising a first surface and a second surface, wherein the buttress further comprises a proximal end and a distal end, wherein the buttress defines a length from the proximal end to the distal end, wherein the buttress further comprises a center region adjacent to a first edge region on one side of the center region and adjacent to a second edge region on the other side of the center region, wherein the buttress is configured to be cut into substantially equal halves by cutting through the center region, and (ii) an adhesive applied to a select one of the first surface and the second surface of the buttress, wherein the adhesive extends from the proximal end of the buttress to the distal end of the buttress, wherein the adhesive is located along the first edge region and the second edge region leaving the center region of the buttress substantially free of the adhesive, wherein the adhesive comprises an asymmetric distribution along the length of the buttress having the adhesive on the first edge region and the second edge region changing between areas of greater adhesive and areas of lesser adhesive, wherein the areas of greater adhesive on the first edge region are located opposite to the areas of lesser adhesive on the second edge region, and wherein the areas of greater adhesive on the second edge region are located opposite to the areas of lesser adhesive on the first edge region; and (b) wherein each of the buttress assemblies are configured to be positioned in an opposing manner with the adhesive of one of the buttress assemblies facing away from the adhesive of the other of the buttress assemblies, wherein when positioned in the opposing manner, the areas of greater adhesive on one of the buttress assemblies are aligned with the areas of lesser adhesive on the other of the buttress assemblies.

20. The apparatus of claim 19, wherein the center region of the buttress comprises one or more slits configured to promote cutting the buttress into halves.

\* \* \* \* \*